United States Patent
Kidon et al.

(10) Patent No.: US 12,279,630 B2
(45) Date of Patent: Apr. 22, 2025

(54) TREATMENT AND PREVENTION OF SEED ALLERGIES

(71) Applicants: Tel HaShomer Medical Research Infrastructure and Services Ltd., Ramat-Gan (IL); The State of Israel, Ministry of Agriculture & Rural Development, Agricultural Research Organization (ARO) (Volcani Center), Rishon-LeZion (IL)

(72) Inventors: Mona Kidon, Rishon-LeZion (IL); Ran Hovav, Mazkeret Batya (IL)

(73) Assignees: Tel HaShomer Medical Research Infrastructure and Services Ltd., Ramat Gan (IL); The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 1123 days.

(21) Appl. No.: 16/961,942

(22) PCT Filed: Jan. 16, 2019

(86) PCT No.: PCT/IL2019/050067
§ 371 (c)(1),
(2) Date: Jul. 14, 2020

(87) PCT Pub. No.: WO2019/142189
PCT Pub. Date: Jul. 25, 2019

(65) Prior Publication Data
US 2020/0345033 A1 Nov. 5, 2020

Related U.S. Application Data

(60) Provisional application No. 62/617,642, filed on Jan. 16, 2018.

(51) Int. Cl.
| | |
|---|---|
| A23J 1/14 | (2006.01) |
| A23J 3/14 | (2006.01) |
| A23J 3/34 | (2006.01) |
| A23L 25/00 | (2016.01) |
| A61K 39/35 | (2006.01) |
| A61K 49/00 | (2006.01) |

(52) U.S. Cl.
CPC .............. *A23J 1/146* (2013.01); *A23J 3/14* (2013.01); *A23J 3/346* (2013.01); *A23L 25/30* (2016.08); *A61K 39/35* (2013.01); *A61K 49/0004* (2013.01)

(58) Field of Classification Search
None
See application file for complete search history.

(56) References Cited

U.S. PATENT DOCUMENTS

| | | | |
|---|---|---|---|
| 9,198,869 B2 | 12/2015 | Walser et al. | |
| 10,086,068 B2* | 10/2018 | Walser | G01N 33/483 |
| 2013/0022718 A1 | 1/2013 | Samadpour | |
| 2014/0363470 A1 | 12/2014 | Koppelman et al. | |
| 2015/0173406 A1* | 6/2015 | Lila | A61K 39/35 |
| | | | 426/632 |

FOREIGN PATENT DOCUMENTS

| | | | |
|---|---|---|---|
| CN | 104066433 | 9/2014 | |
| JP | 2015-500321 | 1/2015 | |
| KR | 1997-0061607 | 6/2000 | |
| RU | 2171040 | 7/2001 | |
| WO | WO-2012123759 A1 * | 9/2012 | ............ A61K 39/35 |
| WO | WO 2019/142189 | 7/2019 | |

OTHER PUBLICATIONS

Mondoulet, L., Paty, E., Drumare, M.F., Ah-Leung, S, Scheinmann, P., Willemot, R.M., Wal, J.M., Bernard, H., 2005. 53:4547-4553. (Year: 2005).*
Chung, S., Butts, C.L., Maleki, S.J., Champagne, E.T., 2003. J Agricul Food Chem. 51: 4273-4277. (Year: 2003).*
Tang, M.L., Ponsonby, A., Orsini, F., Tey, D., Robinson, M., Su, E.L, Licciardi, P., Burks, W., Donath, S., 2014. J Allergy Clin Immunol. Clinical trial. (Year: 2014).*
Wigotzki, M., Steinhart, H., Paschke, A. Determination of the allergenicity of various hazelnut products by immunoblotting and enzyme allergosorbent test inhibition. J. Chromatogr., B: Biomed. Sci. Appl. 2001, 756, 239-48. (Year: 2001).*
Wal, J. M. Thermal processing and allergenicity of foods. Allergy. 2003, 58:727-729. (Year: 2003).*
Beyer, K., Morrow, E., Li, X. M., Bardina, L., Bannon, G. A., Burks, A. W., Sampson, H. A. Effects of cooking methods on peanut allergenicity. J. Allergy Clin. Immunol. 2001, 107, 1077-1081. (Year: 2001).*
Maleki, S.J., Hurlburt, B.K., Structural and Functional Alterations in Major Peanut Allergens Caused by Thermal Processing. 2004. J AOAC Int. 87(6): 1475-1479. (Year: 2004).*
Masthoff, L.J., Hoff, R., Verhoeckx, K.C.M., van Os-Medendorp, H., Michelsen-Huisman, A., Baumert, J.L., Pasmans, S.G., Meijer, Y., Knulst, A.C. A systematic review of the effect of thermal processing on the allergenicity of tree nuts. 2013. Allergy. 68:983-993. (Year: 2013).*
Geroldinger-Simic, M., Zelniker, T., Aberer, W., Ebner, C., Egger, C., Greiderer, A. et al. Birch pollen-related food allergy: clinical aspects and the role of allergen-specific IgE and IgG4 antibodies. 2011. J Allergy Clin Immunol. 127:616-622. (Year: 2011).*

(Continued)

*Primary Examiner* — Daniel E Kolker
*Assistant Examiner* — Maureen Varina Driscoll

(57) ABSTRACT

A composition of matter comprising an extract of a plurality of seeds of an edible plant of interest is disclosed. Use of the composition and methods of generating same are also disclosed.

8 Claims, 10 Drawing Sheets

(56) References Cited

OTHER PUBLICATIONS

Bircher, A.J., Van, M.G., Haller, E., Curty, B.,Frei, P.C. IgE to food allergens are highly prevalent in patients allergic to pollens, with and without symptoms of food allergy. 1994. Clin Exp Allergy. 24:367-374. (Year: 1994).*
Johnson, P.E., Sayers, R.L., Gethings, L.A., Balasundaram, A., Marsh, J.T., Langridge, J.I., Mills, E.N.C.Quantitative Proteomic Profiling of Peanut Allergens in Food Ingredients Used for Oral Food Challenges. 2016. Anal Chem. 88: 5689-5695. (Year: 2016).*
Paik-Ro, O.G., Seib, J.C., Smith, R.L. Seed-specific, developmentally regulated genes of peanut. 2002 Theor Appl Genet 104:236-240. (Year: 2002).*
Geiselhart, S., Hoffmann-Sommergruber, K., Bublin, M. Tree nut allergens. 2018. Molec Immunol. 100:71-81. (Year: 2018).*
Dean, T.P., Immunological responses in peanut allergy. 1998. Clinical & Experimental Allergy, 28: 7-9. (Year: 1998).*
Chung et al. Linking Peanut Allergenicity to the Processes of Maturation, Curing, and Roasting. J Agric Food Chem. 2003. 51: 4273-4277. (Year: 2003).*
Tang et al. Administration of a probiotic with peanut oral immunotherapy: A randomized trial. J Allergy Clin Immunol, 2015. 135(3) 737-745 (Year: 2015).*
Pomes et al. Quantification of Ara h 1 in peanuts: why roasting makes a difference. Clin Exp Allergy, 2006; 36(6):824-830. (Year: 2006).*
Notification of Office Action and Search Report Dated Aug. 17, 2021 From the State Intellectual Property Office of the People's Republic of China Re. Application No. 201980017043.1. (14 Pages).
Search Report and Written Opinion Dated Aug. 13, 2021 From the Intellectual Property Office of Singapore, IPOS Re. Application No. 11202006732W. (11 Pages).
Supplementary European Search Report and the European Search Opinion Dated Sep. 21, 2021 From the European Patent Office R. Application No. 19741509.4. (14 Pages).
Chung et al. "Effect of Ribose on Mature/Immature Raw Peanut Proteins and Their Allergenic Properties", Food and Nutrition Sciences, 2(4) Art. 5681:294-300, Published Online Jun. 2011.
Chung et al. "Linking Peanut Allergenicity to the Processes of Maturation, Curing, and Roasting", Journal of Agricultural Food Chemistry, XP055838283, 51(15): 4273-4277, Published on Web Jun. 18, 2003.
Hollis "X-Ray vision Points to More Efficient Peanut Grading System", FarmProgress, XP055839234, p. 1-4, Jun. 26, 2013.
Van Boxtel et al. "Allergen Ara H 1 Occurs in Peanuts as A Large Oligomer Rather Than as A Trimer", Journal of Agricultural Food Chemistry, 54(19): 7180-7186, Published on Web Aug. 29, 2006.
Van Boxtel et al. "Legumin Allergens From Peanuts and Soybeans: Effect of Denaturation and Aggregation on Allergenicity", Molecular Nutrition & Food Research, XP055212042, 52(6): 674-682, Jun. 2008.

Zhang et al. "Recent Advances in Research on Main Peanut Allergens and Desensitization Methods",.
Zhang et al. "Recent Advances in Research on Main Peanut Allergens and Desensitization Methods", 35(1):312-318, 2014. Chinese with English Abstract.
Decision of Rejection Dated Aug. 29, 2022 From the State Intellectual Property Office of the People's Republic of China Re. Application No. 201980017043.1. (6 Pages).
English Summary Dated Sep. 15, 2022 of Decision of Rejection Dated Aug. 29, 2022 From the State Intellectual Property Office of the People's Republic of China Re. Application No. 201980017043.1. (4 Pages).
Notice of Reason(s) for Rejection Dated Oct. 25, 2022 From the Japan Patent Office Re. Application No. 2020-538672 and Its Translation Into English.(9 pages).
International Preliminary Report on Patentability Dated Jul. 30, 2020 From the International Bureau of WIPO Re. Application No. PCT/IL2019/050067. (8 Pages).
International Search Report and the Written Opinion Dated Mar. 13, 2019 From the International Searching Authority Re. Application No. PCT/IL2019/050067. (10 Pages).
Boote et al. "Growth Stages of Peanut (*Arachis hypogaea* L.)", Peanut Science, 9(1): 35-40, Jan. 1982.
Kang et al. "Temporal and Spatial Expression of the Major Allergens in Developing and Germinating Peanut Seed", Plant Physiology, 144(2): 836-845, Jun. 2007.
Nowak-Wegrzyn et al. "Reactions to Foods", Middleton's Allergy: Principles and Practice, Elsevier Health Sciences, 1 (Chap. 81): 1310-1339, Oct. 18, 2013.
Tao et al. "Sequential Hypoallergenic Boiled Peanut and Roasted Peanut Oral Immunotherapy", Clinical Experimental Allergy,47(11): 1501-1504, Nov. 2017.
Notification of Office Action Dated Apr. 13, 2022 From the State Intellectual Property Office of the People's Republic of China Re. Application No. 201980017043.1 and Its English Summary. (9 Pages).
Williams et al. "A Non-Destructive Method for Determining Peanut Pod Maturity",Penut Science, 8(2): 134-141, Jul. 1, 1981.
Office Action Dated Feb. 25, 2024 From the Israel Patent Office Re. Application No. 276121. (4 Pages).
Notice of Reason(s) for Rejection Dated Apr. 25, 2023 From the Japan Patent Office Re. Application No. 2020-538672 and Its Translation Into English. (6 Pages).
Written Opinion Dated Apr. 19, 2023 From the Intellectual Property Office of Singapore, IPOS Re. Application No. 11202006732W. (7 Pages).
Examination Report Dated Nov. 3, 2023 From the Australian Government, IP Australia Re. Application No. 2019210146. (5 Pages).

\* cited by examiner

TREATMENT AND PREVENTION OF SEED ALLERGIES

RELATED APPLICATIONS

This application is a National Phase of PCT Patent Application No. PCT/IL2019/050067 having International filing date of Jan. 16, 2019, which claims the benefit of priority under 35 USC § 119 (e) of U.S. Provisional Patent Application No. 62/617,642 filed on Jan. 16, 2018. The contents of the above applications are all incorporated by reference as if fully set forth herein in their entirety.

FIELD AND BACKGROUND OF THE INVENTION

The present invention, in some embodiments thereof, relates to a method of treating and preventing allergies to seeds of edible plants and, more particularly, but not exclusively, to peanuts.

Food allergy has been dubbed "the plague of the 21st century" and has risen as the 'second wave' of the allergy epidemic. Food allergy is an adverse health effect arising from a specific immune response that occurs reproducibly on exposure to a given food. Based on recent studies, the prevalence of clinical (OFC proven) food allergy in preschool children in some developed countries is now as high as 10%. In large and rapidly developing countries in Asia, such as China, the prevalence of food allergy in infants is now around 4% and rates of food allergy are now following the steep gradient of economic transition.

As part of the allergy food epidemic but even more worrisome, over the last 20 years, peanut allergy has become a global public health problem affecting 1.5% to 3% of children. It is considered one of the most "dangerous" of the food allergies with significant accidental exposures and life threatening reactions and fatalities. In most children, it does not spontaneously resolve, i.e. is a lifetime threat and therefore finding better therapeutic options is now a global unmet need. The current management of this life threatening chronic disease, i.e. complete avoidance of peanut containing foods and constant availability of an epinephrine auto-injection, still leaves patients and families with an abysmally low quality of life, and a significant incidence of morbidity due to accidental exposures as well as rare but significant fatal outcomes.

In the past few years, oral immunotherapy (OIT) with peanuts has emerged as an option for the treatment of allergic patients. Different protocols of peanut OIT have been published with varying degrees of success [Sun J, et al., Allergy Asthma Proc 2014; 35:171-7]. However all are rife with severe adverse reactions during all phases of treatment, seem to achieve only a state of desensitization, i.e. a state of temporary antigen hyporesponsiveness that is maintained only as long as the child continues daily consumption of the peanut dose and most children do not achieve permanent tolerance. When dosing is interrupted or discontinued, the protective effect of desensitization is lost, and even during the treatment, augmentation factors such as viral infection or exercise may trigger reactions to the previously tolerated maintenance dose [Nurmatov U, et al., Allegy, 2017; 72:1133-47]. The ubiquitous side effects of the procedure are such that most OIT programs do not enroll children under the age of 4-6 years, leaving out the youngest and most vulnerable patients afflicted with the allergy. The exact mechanism of desensitization is not known, but associated immunologic changes include decreased reactivity of mast cells (measured with skin prick test reactivity) and basophils, increased food-specific serum and salivary $IgG_4$ and IgA antibodies, and initially increased but eventually decreased serum food-specific IgE antibodies.

Observational data as well as non-blinded studies have shown that children with cow's milk allergy (CMA) or egg allergy (EA), capable of consuming extensively heated and baked milk/egg proteins safely, have a speedier resolution of their allergy, if they incorporate significant amounts of these proteins into their diet, [Nowak-Wegrzyn A, et al., J Allergy Clin Immunol 2008; 122:342-7, 7 e1-2]. The mechanism of permanent tolerance is not known, but it may involve development of regulatory T cells followed by anergy and/or deletion of effector T cells. Patients undergoing spontaneous development of tolerance to a previously allergenic food, manifest gradual decreases in their food specific IgE, increases in specific IgG and increase in a subset of allergen specific T regulatory cells, eventually developing tolerance in the course of the natural history of CMA and EA. Typically, heat denaturation of allergenic proteins from animal sources causes abrogation of conformational allergic epitopes recognized by most species of specific IgE in allergic patients, so that the allergic response to these foods is severely diminished [Burton O T, et al., Immunity 2014; 41:141-51]. This effect of heat treatment is enhanced by the presence of a wheat matrix, i.e. preparation in cookies or waffles and seems to work differentially on specific proteins [Bloom K A, et al., Pediatr Allergy Immunol 2014; 25:740-6]. Allergen specific T cells however have the ability to recognize short linear epitopes from the same proteins that are unchanged by heating or cooking. Inhibition of the IgE mediated allergic response during allergen ingestion leads to reversal of established food allergy and induction of regulatory T cells [Burton O T, et al., Immunity 2014; 41:141-51].

In contrast to animal-based foods, allergenic proteins from seeds, including peanuts, are relatively stable to heat denaturation. In some circumstances, such as dry roasting of peanuts, the allergenicity of the major allergens is actually enhanced and not diminished [Vissers Y M, et al., Clin Exp Allergy 2011; 41:1631-42]. Even boiling/cooking while capable of decreasing the solubility of major peanut allergens Ara h1 and Ara h2 does not produce hypoallergenic material from peanuts [Comstock S S., et al., PLoS One 2016; 11:e0157849].

Additional background art includes US Patent Application No. 20150173406 and U.S. Pat. No. 9,198,869.

SUMMARY OF THE INVENTION

According to an aspect of the present invention there is provided a composition of matter comprising an extract of a plurality of non-mature seeds of an edible plant of interest, wherein the seeds are at a developmental stage such that the extract has a decreased allergenicity following processing compared to the allergenicity of an extract of fully mature seeds of the plant following the processing in at least 25% of subjects characterized as being allergic to fully mature seeds of the plant, wherein the developmental stage is such that the seed comprises at least 50% of an amount of at least one allergenic protein which is comprised in the fully mature seed, wherein the composition of matter is essentially devoid of fully mature seeds of the edible plant, wherein the allergenicity is assayed by measuring the allergic reaction in the subject following topical application.

According to an aspect of the present invention there is provided a composition of matter comprising an extract of a plurality of seeds of an edible plant of interest, wherein the seeds are at a developmental stage which corresponds to an increased tendency of at least one allergenic protein of the seeds to undergo denaturation following processing compared to the tendency of the at least one storage protein of a fully mature seed to undergo denaturation following the processing, wherein the at least one allergenic protein of the seed is denatured in the extract, wherein the composition of matter is essentially devoid of non-denatured allergenic proteins of fully mature seeds.

According to an aspect of the present invention there is provided a food product comprising the composition of matter described herein.

According to an aspect of the present invention there is provided a method of generating a composition of matter comprising an extract of seeds of an edible plant, the method comprising:

(a) selecting seeds of the edible plant which are at a developmental stage which correspond to a reduced allergenicity of at least one allergenic protein of the seeds following processing compared to the allergenicity of the at least one allergenic protein of fully mature seeds of the edible plant following the processing in at least 25% of subjects characterized as being allergic to fully mature seeds of the plant, wherein the developmental stage is such that the seed comprises at least 50% of an amount of at least one allergenic protein which is comprised in the fully mature seed;

(b) isolating the seeds selected according to step (a) so as to generate a collection of seeds which is devoid of mature seeds of said edible plant, and (c) drying said collection of seeds, thereby generating the composition.

According to an aspect of the present invention there is provided a method of generating a composition of matter comprising an extract of seeds of an edible plant, the method comprising:

(a) selecting seeds of the edible plant which are at a developmental stage which correspond to an increased tendency of at least one allergenic protein of the seeds to undergo denaturation following processing compared to the tendency of the at least one allergenic protein of a fully mature seed to undergo denaturation following the processing; and (b) isolating the seeds selected according to step (a) so as to generate a collection of seeds which is devoid of mature seeds of said edible plant, (c) processing said collection of seeds for a length of time that denatures said at least one allergenic protein, thereby generating the composition.

According to an aspect of the present invention there is provided a composition of matter generated according to the method described herein.

According to an aspect of the present invention there is provided a method of inducing desensitization to seeds in an allergic subject comprising providing the composition described herein to the subject using a treatment regimen that induces desensitization to seeds in the allergic subject, thereby inducing desensitization to seeds in the allergic subject.

According to an aspect of the present invention there is provided a method of selecting a subject for desensitization treatment to a seed comprising:

(a) contacting the skin of the subject with the composition of matter described herein;

(b) measuring the allergic response to the composition of matter on the skin of the subject; and (c) comparing the allergic response measured in step (b) to the allergic response of the subject to a composition which comprises an extract of mature seeds of an edible plant, wherein a reduction in the allergic response in the subject is indicative that the subject should be selected for a desensitization treatment to a seed.

According to an aspect of the present invention there is provided a method of determining if a subject is allergic to a seed comprising:

(a) contacting the skin of the subject with the composition of matter described herein; and (b) analyzing the skin of the subject, wherein a non-allergenic response on the skin of the subject is indicative that the subject is not allergic to the seed.

According to an aspect of the present invention there is provided a method of preventing allergenicity of a subject to seeds comprising providing to the subject the composition described herein, under conditions that prevents allergenicity of the subject to the seeds.

According to an aspect of the present invention there is provided an isolated denatured storage protein of a seed of a plant.

According to embodiments of the present invention, at least one allergenic protein of the seed is denatured in the extract.

According to embodiments of the present invention, the developmental stage is such that the seed comprises at least 50% of an amount of at least one allergenic protein comprised in the fully mature seed.

According to embodiments of the present invention, the allergenic protein comprises a storage protein.

According to embodiments of the present invention, the processing comprises a heat treatment.

According to embodiments of the present invention, the edible plant of interest is a pod-bearing plant.

According to embodiments of the present invention, the edible plant of interest is a tree.

According to embodiments of the present invention, the seeds are peanut seeds.

According to embodiments of the present invention, the seeds are walnut seeds.

According to embodiments of the present invention, the developmental stage is such that the seeds occupy between 30-70% of the pod volume.

According to embodiments of the present invention, the developmental stage is such that the seeds occupy between 40-60% of the pod volume.

According to embodiments of the present invention, the peanut is harvested no more than 75 days post planting.

According to embodiments of the present invention, the at least one allergenic protein is selected from the group consisting of Arah 1, Arah 2, and Arah 3.

According to embodiments of the present invention, the composition is sterile.

According to embodiments of the present invention, the composition is in a powder form.

According to embodiments of the present invention, the composition is hypoallergenic in a subject that is allergic to the native form of the at least one storage protein.

According to embodiments of the present invention, the allergenicity of the subject is measured following topical application of the composition.

According to embodiments of the present invention, the food is cooked.

According to embodiments of the present invention, the food further comprises wheat.

According to embodiments of the present invention, the food is raw.

According to embodiments of the present invention, the food is a baby food or infant formula.

According to embodiments of the present invention, the method further comprises processing the seeds for a length of time that reduces the allergenicity of the at least one allergenic protein following the drying.

According to embodiments of the present invention, the method further comprises processing the seeds following step (a) and prior to step (b) to generate dried seeds.

According to embodiments of the present invention, the method further comprises grinding the dried seed prior to step (b).

According to embodiments of the present invention, the processing comprises heating.

According to embodiments of the present invention, the selecting is effected manually.

According to embodiments of the present invention, the selecting is effected using x-ray technology.

According to embodiments of the present invention, the seeds are harvested at a time when more than 3% of the seeds of a crop are of the developmental stage.

According to embodiments of the present invention, the composition is provided orally.

According to embodiments of the present invention, the treatment regimen comprises initially providing the composition as a cooked product.

According to embodiments of the present invention, the treatment regimen subsequently comprises providing the composition as a raw product if the subject displays tolerance to the cooked product.

According to embodiments of the present invention, the subject is selected for treatment by evaluating the response to topical application of the composition.

According to embodiments of the present invention, the composition is provided in an amount between 0.1-2 gr of protein per week.

According to embodiments of the present invention, the subject is an infant.

According to embodiments of the present invention, the composition is a milk formula or baby food.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
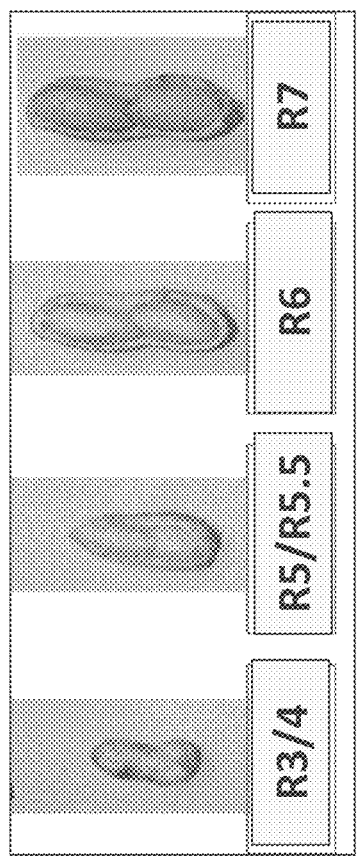
FIG. 1 illustrates peanut's seed developmental stages (cv. Hanoch).

The present invention, in some embodiments thereof, relates to a method of treating and preventing allergies to seeds of edible plants and, more particularly, but not exclusively, to peanuts.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Because peanut allergies can present life-threatening consequences, there is intense interest in developing therapeutic strategies that could reduce the danger and severity of the allergic reaction to peanuts in sensitive patients.

Oral immunotherapy (OIT), which involves highly regulated administration, in a clinical setting, of very small doses of allergenic proteins is a strategy that has recently shown promise for desensitizing some allergic patients, so as to attenuate a potentially life threatening anaphylactic reaction to a chance ingestion of allergenic foods. However, OIT carries significant risks and side effects, including gastrointestinal problems, wheezing, and even anaphylactic shock; these barriers preclude rapid dissemination of the technology beyond highly controlled clinical settings.

Various processing-based strategies are being investigated for the potential to modify/improve the allergenic profiles of allergic proteins. Some examples include heat induced aggregation, enzymatic hydrolysis and controlled Maillard type modifications.

In contrast to animal-based foods, allergenic proteins from seeds (e.g. peanuts), are relatively stable to heat denaturation. In some circumstances, such as dry roasting of peanuts, the allergenicity of the major allergens is actually enhanced and not diminished. Even boiling/cooking while capable of decreasing the solubility of major peanut allergens Arah1 and Arah2 does not produce hypoallergenic material from peanuts.

The present inventors have come to the understanding that major peanut protein allergens as well as major protein allergens from seeds such as sesame and tree nuts, are organized in the mature plant in functional structures that enhance their resistance to denaturation efforts. Without being bound to theory, the present inventors surmised that if abrogation of the conformational epitopes of protein allergens could be performed, since more than 90% of allergen-specific IgE species recognize these non-linear structures, then treatment with the "abrogated" material should be both safe and effective. To do this, the present inventors propose using seeds (such as peanuts) at a particular immature developmental stage in specific cultivars, where allergenic proteins are still amenable to heat denaturation during boiling, cooking and baking. The present inventors propose that using this strategy, it should be possible to develop a safe protocol of immunotherapy in seed allergic individuals that will enable the treatment of young children, which should lead to a more permanent change in the immune system, akin to the development of tolerance.

Whilst reducing the present invention to practice, the present inventors have identified a developmental stage based on measurable physical properties in peanut cultivars that enables heat denaturation of allergenic proteins from peanuts (FIG. 1).

Whilst further reducing the present invention to practice, the present inventors manufactured a desiccated powder composition containing these proteins and developed a process of boiling, heating and cooking of these immature peanuts that enables safe administration to children with proven peanut allergy (FIG. 2).

In a clinical study, each of the 15 peanut-allergic children enrolled have shown an improved allergic response to peanuts by oral immunotherapy with this composition to varying degrees—see Example 4.

The present inventors also demonstrated that the composition is useful for correct diagnosis of peanut allergy. The skin prick allergic reaction, i.e. the standard test for the immediate diagnosis of food allergy, using this composition was more correlative to the level of Arah2 antibody than the skin prick reaction using a composition from mature peanuts.

Taken together, according to the teachings described herein, compositions comprising seeds of edible plants of a particular developmental stage can be used to accurately diagnose plant associated food allergies and treat allergic subjects i.e. perform food allergy immunotherapy. The present teachings further suggest that such compositions may be useful for building up tolerance to edible seeds thereby preventing the development of plant derived food allergies in babies and/or infants.

Thus, according to a first aspect of the present invention, there is provided a composition of matter comprising an extract of non-mature seeds of an edible plant of interest, wherein the seeds are at a developmental stage such that the extract has a decreased allergenicity following processing compared to the allergenicity of an extract of fully mature seeds of the plant following the processing in at least 25% of subjects characterized as being allergic to fully mature seeds of the plant, wherein the developmental stage is such that the seed comprises at least 50% of an amount of at least one allergenic protein which is comprised in the fully mature seed, wherein the composition of matter is devoid of fully mature seeds of the edible plant, wherein the allergenicity is assayed by measuring the allergic reaction in the subject following topical application.

According to another aspect of the present invention there is provided a composition of matter comprising an extract of a plurality of seeds of an edible plant of interest, wherein the seeds are at a developmental stage which corresponds to an increased tendency of at least one allergenic protein of the seeds to undergo denaturation following processing compared to the tendency of the at least one storage protein of a fully mature seed to undergo denaturation following the processing, wherein the composition of matter is essentially devoid of non-denatured allergenic proteins of fully mature seeds.

The term "antigen" refers to a molecule or part thereof, usually a protein which elicits, induces, stimulates, or enhances an immune response in the immune system of an exposed animal (e.g., human).

The term "allergen", as used herein, refers to an antigen which induces a specific immune response i.e. the development of enhanced sensitivity or a hypersensitivity to the antigen, but the antigen itself is not typically innately harmful. An allergen is therefore a particular type of antigen that can cause development of enhanced or increased sensitivity or hypersensitivity in a subject. For example, an allergen can elicit production of IgE antibodies in predisposed subjects.

The term "allergy" as used herein refers to a hypersensitivity disorder of the immune system.

The term "allergenicity" as used herein refers to the potential of an allergen to cause an allergic reaction.

An allergic response includes but is not limited to an allergic reaction, hypersensitivity, an inflammatory response or inflammation. In certain embodiments allergic response may involve one or more of cell infiltration, production of antibodies, production of cytokines, lymphokines, chemokines, interferons and interleukins, cell growth and maturation factors (e.g., differentiation factors), cell proliferation, cell differentiation, cell accumulation or migration (chemotaxis) and cell, tissue or organ damage or remodeling.

Allergic responses can occur systemically, or locally in any region, organ, tissue, or cell. In particular aspects, an allergic response occurs in the skin, the upper respiratory tract, the lower respiratory tract, pancreas, thymus, kidney, liver, spleen, muscle, nervous system, skeletal joints, eye, mucosal tissue, gut or bowel.

The term "extract" as used herein refers to a composition derived from the edible portion of a seed (i.e. not derived from the non-edible portion of a seed, such as a shell). It will be appreciated that in certain plants at an immature stage there may not be a definitive separation between what will become the non-edible portion (i.e. a shell) and the seed within, and the extract therefore refers to the whole seed.

In one embodiment, the extract is a polar extract (i.e. extracted using a polar solvent). This may be advantageous since polar or water based extraction of proteins lacks the ability to include fat soluble proteins, that in some plants such as sesame and peanuts may have a major role in eliciting hypersensitivity/allergy.

In another embodiment, the extract is a non-polar extract (i.e. extracted using a non-polar solvent).

In still another embodiment, the extract is a protein extract.

In still another embodiment, the extract is a whole seed extract.

In still further embodiments, the extract may be devoid of the shell.

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower, petal, fruit, any storage organ (e.g., tuber, bulb, corm, false stem, leaves etc.). The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be within the plant, in organ culture, tissue culture, or cell culture. The term "plant part" as used herein refers to a plant organ or a plant tissue.

The term "edible plant" refers to any plant or part thereof which is suitable for mammalian consumption.

The plants are typically grown under conditions that suit the particular variety and the growth of the seed. It will be appreciated that the plant may be treated with hormones or hormone releasing compounds to enhance growth. Such hormones include, but are not limited to auxin, gibberellin, cytokinin, ethylene, and abscisic acid. According to a particular embodiment, the hormone is ethylene.

As used herein, the term "seeds" refers to seeds of trees (i.e. nuts), seeds of pod-bearing plants (i.e. legumes) or seeds of fruit (such as sesame) which comprise allergens (molecules, mostly but not restricted to proteins, such as storage proteins, that can cause an allergic reaction in humans). Examples of tree nuts include, but are not limited to walnut, pecan, almond, hazelnut, cashew, pistachio and Brazil nut. Other exemplary legumes include, but are not limited to alfalfa, clover, peas, beans, chickpeas, lentils, lupin bean, mesquite, carob, soybeans, peanuts and tamarind.

Other exemplary seeds contemplated by the present invention include, but are not limited to chestnuts, cocoa seeds, cotton seeds, flax seeds, Macadamia nuts, mustard, pine nuts, poppy seeds, pumpkin seeds and sunflower seeds.

According to a particular embodiment, the seed is a peanut—e.g. of the species *Arachis hypogaea*.

Exemplary subspecies and varieties of *Arachis hypogaea* contemplated by the present invention include the subspecies *fastigiata* Waldron (exemplary varieties include, but are not limited to var. *aequatoriana* Krapov. & W. C. Greg; var. *fastigiata* (Waldron) Krapov. & W. C. Greg; var. *peruviana* Krapov. & W. C. Greg; and var. *vulgaris* Harz) and the subspecies *hypogaea* L. (exemplary varieties include *hirsuta* J. Kohler and var. *hypogaea* L).

According to a particular embodiment, the variety is the Hanoch variety (see Gupta et al., Plant Sci. 2016 Jul; 248:116-27. doi: 10.1016/j.plantsci.2016.04.014. Epub 2016 Apr. 28).

It will be appreciated that the composition of matter of this aspect of the present invention may comprise extracts from more than one seed type. Thus, for example, the present invention contemplates compositions comprising extracts of 2 different types of peanuts or alternatively two different seeds entirely, such as peanuts and almonds, peanuts and walnuts, peanuts and cashews.

The phrase "non-mature seeds" or "immature seeds" as used interchangeably, refers to a developmental stage of the seed, wherein the seed occupies less than the pod volume it typically fills at full maturity. In one embodiment, the non-mature seed is one which shows signs of degradation at room temperature after 24 hours.

The exact developmental stage of the seeds in the composition is selected such that the seed has a decreased allergenicity following processing compared to the allergenicity of an extract of fully mature seeds of the plant following the processing, as measured in allergic subjects.

Thus, for example in one embodiment, the seeds (e.g. peanuts) that are used in the composition are at a stage such that they occupy less than 80%, less than 70% e.g. between 30-90% the pod volume, 30-80% the pod volume, 30-70% of the pod volume, 40-70% of the pod volume, 30-60% of the pod volume or more specifically 40-90% of the pod volume, depending on the particular variety or cultivar.

For peanuts, the present inventors have found that the optimal stage is at R5 or R5.5—see for example Boote, Peanut Science (1982) 9, 35-40, the contents of which being incorporated herein by reference.

Without being bound to theory, the present inventors propose at this stage the allergenic proteins comprises in the seed are more susceptible to denaturation than at the mature stage.

This susceptibility may correlate with a harvesting date of no more than 60 days post planting, 65 days post planting, 70 days post planting, 75 days post planting or even 80 days post planting, depending on the particular variety or cultivar.

Preferably the seeds are harvested at a time when more than 1%, 2%, 3%, 5%, 10%, 15%, 20%, 25%, 30%, 35%, 40%, 45%, 50%, 55%, 60%, 65%, 70%, 75%, 80%, 85%, 90%, 95% of the seeds of the plant are of the required developmental stage.

It will be appreciated that the stage should also correspond to one wherein there is a sufficient quantity of allergenic molecules (e.g. proteins) that can bring about desensitization in an allergic subject. Thus for example, the stage should be selected such that there is at least 20%, 30%, 40%, 50%, 60%, 70%, 80%, 90% the amount of at least one allergenic protein that is present in the corresponding mature seed.

In some embodiments, the allergenic protein belongs to a protein family that is known or suspected to induce allergy or specific hypersensitivity in one or more individuals. In a particular embodiment, the allergenic protein is a storage protein. Examples of protein families known or suspected to induce allergy or specific hypersensitivity in one or more individuals may include, without limitation, the prolamin superfamily, the cupin superfamily, the profilins, and Bet v-1-related proteins. Other information regarding allergenic proteins and families thereof may be found in Middletons Allergy 2013, Chapter 81, Reactions to Food, pages 1310-1339

Care should be taken when preparing the composition of matter of this aspect of the present invention that no mature seeds contaminate the preparation. In one embodiment, the composition of matter is essentially devoid of fully mature seeds. In another embodiment, the composition of matter is essentially devoid of non-denatured allergenic proteins of the fully mature seeds. According to a particular embodiment, 100% of the seeds of the composition are of the required developmental stage, at least 99% of the seeds of the composition are of the required developmental stage, at least 98% of the seeds of the composition are of the required developmental stage, at least 97% of the seeds of the composition are of the required developmental stage, at least 96% of the seeds of the composition are of the required developmental stage, at least 95% of the seeds of the composition are of the required developmental stage, at least 94% of the seeds of the composition are of the required developmental stage, at least 93% of the seeds of the composition are of the required developmental stage, at least 92% of the seeds of the composition are of the required developmental stage, at least 91% of the seeds of the composition are of the required developmental stage, at least 90% of the seeds of the composition are of the required developmental stage.

To ensure that the extract is devoid of mature seeds, the seeds may be sorted manually post-harvesting by visual inspection (i.e. using visible light) or by using other forms of electromagnetic radiation and imaging techniques, such as, but not limited to microwave, infrared light, ultraviolet light, X-rays or gamma rays which penetrate the pods, such that shelling is not necessary for the sorting process. In one embodiment, X-ray technology is used.

In another embodiment, a variety of plant is used that shows an increased tendency for seeds in the same pod to be at the same developmental stage. Thus, for example a variety of peanut plant can be used wherein at a particular time, more than 50% of the pods of the plant comprise two seeds of the required stage, more than 60% of the pods of the plant comprise two seeds of the required stage, more than 70% of the pods of the plant comprise two seeds of the required stage, more than 80% of the pods of the plant comprise two seeds of the required stage, more than 90% of the pods of the plant comprise two seeds of the required stage.

In one embodiment, in order to generate the composition described herein, the seeds are harvested and separated from their non-edible shells under conditions that do not affect the rate and/or amount of decay of the seeds. Thus, for example the seeds should be shelled and optionally stored at a temperature of less than 10° C.—for example shelled at 4° C. and optionally stored at −20° C.

Optionally, the seeds may be subjected to a pre-processing procedure prior to the allergenicity-reducing procedure, which is further described herein below. This pre-processing procedure may include, but not limited to aliquoting into a measured amount (e.g. about 1-10 g of total protein; 1-4 g of total protein, 2 g of total protein); drying (e.g. freeze-drying, dessicating or lyophilization); and/or grinding into a powder.

In one embodiment, the drying stage is effected at a temperature below 50° C. In another embodiment, the drying stage is effected at a temperature below 40° C. The drying should be such that the seed loses at least 10%, 20%, 30%, 40%, 50%, 60%, 70%, 80% or more of its water content.

Thus, the present invention contemplates a collection of seeds which are at the required stage. The collection is essentially devoid of seeds at a stage later than the required stage. The collection is essentially devoid of seeds of an earlier stage. The seeds may be shelled and/or dried. The number of seeds may be greater than 50, 100, greater than 200, greater than 300, greater than 400 or greater than 500. The seeds may be in a powder form. The collection may be placed in a container—e.g. bag, box, crate, bottle etc.

Other pre-processing procedures contemplated by the present inventors include lyophilizing, cutting, mincing, homogenizing and liquidizing and any other food industry derived procedures that do not interfere with the protein moiety such as cleaning, pasteurization, etc.

In one embodiment, the composition is generated by:
(a) harvesting plants at an optimal time for enrichment of seeds of the indicated developmental stage;
(b) immediate cooling of the seeds (e.g. refrigeration in low environmental humidity);
(c) shelling;
(d) selection of seeds of the required developmental stage;
(e) processing to separate water from biological matter (e.g. lyophilization or freeze drying);
(f) grinding to a fine powder/flour for subsequent use.

Aliquoting of the seeds can be performed at any stage, for example between steps (d) and (e) or following step (f).

Following selection and optional processing the seeds may be characterized using methods known in the art including, but not limited to high-performance liquid chromatography, enzyme-linked immunosorbent assay, and assaying for protein content. Exemplary proteins that may be analyzed include Ara h1, Ara h2, and Ara h6 antigens. Additional proteins that may be analyzed include, but are not limited to Ara h3 and Ara h8.

Following selection of the correct stage (either by eye or using the technology described herein above) and optional pre-processing, the seeds typically undergo processing so as to reduce their allergenicity (for example by denaturation of the allergenic proteins), as further described below.

Thus, according to further aspects of the present invention there is provided a composition of matter comprising an extract of a plurality of non-mature seeds of an edible plant of interest, wherein said seeds are at a developmental stage such that the extract has a decreased allergenicity following processing compared to the allergenicity of an extract of fully mature seeds of said plant following said processing in at least 25% of subjects characterized as being allergic to fully mature seeds of said plant, wherein said developmental stage is such that the seed comprises at least 50% of an amount of at least one allergenic protein which is comprised in said fully mature seed, wherein said composition of matter is essentially devoid of fully mature seeds of said edible plant, wherein said allergenicity is assayed by measuring the allergic reaction in said subject following topical application, wherein at least one allergenic protein of said seed is denatured in the extract.

According to still another aspect of the present invention there is provided a composition of matter comprising an extract of a plurality of seeds of an edible plant of interest, wherein said seeds are at a developmental stage which corresponds to an increased tendency of at least one allergenic protein of said seeds to undergo denaturation following processing compared to the tendency of said at least one storage protein of a fully mature seed to undergo denaturation following said processing, wherein said at least one allergenic protein of said seed is denatured in the extract, wherein said composition of matter is essentially devoid of non-denatured allergenic proteins of fully mature seeds.

Reduction of allergenicity may be carried out using any method known in the art. In one embodiment, reduction of allergenicity is carried out by heating the seeds. In another embodiment, reduction of allergenicity is carried out by applying pressure to the seeds. In still other embodiments, reduction of allergenicity is carried out by enzymatic proteolysis. Combinations of these processes are also contemplated. Preferably, the process brings about denaturation of the allergenic proteins (e.g. storage proteins) in the seeds.

The term "denaturation" refers to a change in the 3D and/or 4D conformation of a protein or peptide sequence. In one embodiment, the protein or peptide changes from a 3D conformation to a 2D conformation—i.e. becomes linear.

Examples of allergenic storage proteins in peanuts include Arah 1, Arah 2, and Arah 3.

For peanuts, the present inventors have shown that a heating process of 2 hours at 95° C. is sufficient for a reduction in allergenicity (e.g. as measured by the skin prick allergic reaction) in at least 25% of subjects characterized as being allergic to fully mature peanuts.

It will be appreciated that other heating protocols are also contemplated such as temperatures between 50-500° C. or higher for a length of time between 1 hour-24 hours or longer.

As mentioned, the procedure should be such that the composition shows a reduction in allergenicity of subjects characterized as being allergic to fully mature seeds.

A "subject characterized as being allergic to fully mature seeds", refers to a subject that shows clinical symptoms of IgE mediated hypersensitivity on consuming or coming in direct and sometimes indirect contact with the mature seeds. In one embodiment, the subject with a peanut allergy may display peanut-specific serum IgE, i.e. IgE which specifically binds to peanut proteins. However, it should be understood that even if individuals do not exhibit detectable levels of peanut specific IgE (as measured by any technique in serum or a positive immediate SPT as measured in vivo on the subject's skin), they nevertheless should be understood to fall within the scope of the definition of those being allergic if they develop an immediate allergic reaction upon exposure to the food.

In one embodiment, an allergic subject is one in which has been characterized as such according to standard clinical criteria. Standard clinical criteria may include for example, a history of a type-1 hypersensitivity reaction which is temporally related to allergen (e.g. peanut) ingestion (e.g. hives, swelling, wheezing, abdominal pain, vomiting, breathlessness), and the presence of allergen-specific IgE by positive skin prick test (wheal diameter>/=3, 4 or 5 mm) or ImmunoCap serum g>0.35 kU/l.

The compositions of this aspect of the present invention (either prior to denaturation or following denaturation) may be in any form—e.g. a dried form (e.g. powder or flour), a liquid form or a semi-solid form—e.g. a butter or chewing gum.

In a preferred embodiment, the composition is sterile.

In one embodiment, the compositions described herein are formulated for oral administration.—e.g. as a capsule, a tablet, a mini-tablet, a powder, or a sprinkle.

In another embodiment, the compositions are provided as a spray or sublingual application or emollient for skin application or any form of application that presents a composition derived from edible immature plant seeds to the immune system of an individual.

In a particular embodiment, the composition (either prior to denaturation or following denaturation) is administered in a pharmaceutical composition where it may be mixed with suitable carriers and/or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the seed composition accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a subject.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a subject. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

In another embodiment, the compositions (either prior to denaturation or following denaturation) are provided in a food product.

The food product may be supplemented with flavourings to mask the taste of the composition described herein. Suitable food flavourings are well-known in the art and include sugar, mint, vanilla and orange essence.

The food product may be supplemented with preservatives, stabilizing agents, fillers. colorings and sweeteners in accordance with standard food production techniques.

The food product may be cooked (e.g. baked, fried, grilled) or raw.

Exemplary food products include infant formula, baby food, protein bars and protein drinks.

Exemplary baked products include a biscuit, a cookie or a cake. Exemplary fried products include a pancake or waffle. Exemplary raw food products include a spread.

In one embodiment, the food product also comprises wheat. In another embodiment, the food product is devoid of wheat.

The compositions described herein have a myriad of uses, each of which will be discussed below.

1. Desensitization.

According to one aspect of the present invention there is provided a method of inducing desensitization to seeds in an allergic subject comprising providing the composition (denatured, or non-denatured) described herein to the subject using a treatment regimen that induces desensitization to seeds in said allergic subject, thereby inducing desensitization to seeds in the allergic subject.

The term "desensitization", as used herein refers to the increasing of tolerance to one or a group of allergens in a subject classified as being allergic to that seed.

As used herein, the term "tolerance" refers to a) a decreased or reduced level of a specific immunological response (thought to be mediated at least in part by an antibody); b) a delay in the onset or progression of a specific immunological response; or c) a reduced risk of the onset or progression of a specific immunological response to an antigen or allergen. "Specific" immunological tolerance occurs when tolerance is preferentially invoked against certain antigens (allergens) in comparison with other antigens (allergens). Tolerance is an active antigen dependent process and differs from non-specific immunosuppression and immunodeficiency.

An increase, improvement, enhancement or induction of "tolerance" refers to a decrease, reduction, inhibition, alleviation, suppression, or limiting or controlling or clearing of specific immunological reactivity to an antigen as compared to reactivity to the antigen in a previous exposure to the same antigen. Thus in certain embodiments, a method or use of inducing tolerance in a subject to an allergen includes elimination of an allergic response of the subject to the allergen. Immunological tolerance in a subject to an allergen can also be reflected by reducing the occurrence, frequency, severity, progression, or duration of an allergic response of the subject to the antigen or allergen.

While tolerance can refer to non-reactivity to an antigen or allergen, tolerance need not be complete non-reactivity and can only be partial, and in any event is reflected by a decrease, inhibition, suppression or reduction in specific immunological reactivity to an antigen or allergen as compared to reactivity to the antigen or allergen in a previous exposure to the same antigen or allergen (or epitope thereof). Thus, in another embodiment, a method or use of inducing immunological tolerance in a subject to an allergen includes stabilizing or maintaining the level of an allergic response in the subject to the allergen.

Subjects that may be treated are typically mammalian subjects such as humans. In one embodiment, the subject is below 18 years old. Subjects may be selected based on their response to topical application of the composition. Thus for example, the response to topical application of the composition may be compared with the response to topical application of a mature seed composition, when a reduction in wheal size is indicative that the subject is amenable to treatment. Preferably, the diameter of the wheal is reduced by at least 10%, 20%, 30%, 40% or greater after topical application of the immature seed composition as compared to following topical application of the mature seed composition.

As described above, compositions for use as described herein may be formulated in unit dose formulations which contain a defined amount of antigenic protein.

The initial dose of the composition which is administered to the individual may be about 2 mg of protein or less per week. For example, the initial dose may be 0.1 mg, 0.5 mg, 1 mg, 2 mg per week, but higher doses can be elected on an individual basis.

Preferably, the subject is subjected to the composition on a daily basis—for example, once a day, twice a day or more. Also the subject may be subjected to the composition regularly such as 3 times a week, once a week or once a month, depending on the stage of desensitisation, the initial response and the vehicle chosen. It will be appreciated that the administration of doses can be divided in any way per day and up to the recommended total weekly dose.

In one embodiment, the dosage of the composition is increased incrementally during the course of the treatment regimen. For example, the daily or weekly oral dose of the composition may be increased at intervals of at least 2 weeks, 4 weeks, 6 weeks, 8 weeks, 12 weeks or 16 weeks in a series of particular increments. In another embodiment, the dosage of the composition. is maintained fixed during the course of the treatment regimen and only the processing incrementally reduced at intervals of at least 2 weeks, 4 weeks, 6 weeks, 8 weeks, 10 weeks, 12. weeks or 16 weeks, etc.

The daily or weekly oral dose may be increased if the patient has not suffered from an adverse allergic reactions, required anti-allergy treatment, suffered from concurrent illness or received a vaccination during the administration of the dose increment.

If the subject has suffered from an adverse allergic reaction, received anti-allergy treatment or suffered from a concurrent illness during dose increment, then the previous dose may be maintained for at least 1, 2, 3 or 4 additional weeks before further incremental dose increases.

In another embodiment, the conformational state of the allergenic protein may be changed throughout the course of the treatment regime. Thus, for example the initial composition may be provided after it has been both fried and baked (e.g. as a cookie). Frying may be carried out in a suitable oil (for example, vegetable oil). Baking may be carried out at a temperature between 150-200° C., for a length of time between 5 minutes to 1 hour. An exemplary treatment is 180° C. for 20 minutes. Subsequently, in a later stage, the composition may be provided after it has been fried only (e.g. as a pancake or waffle). Subsequently, in a later stage, the composition may be provided as a cooked spread and finally, the composition may be provided as a non-cooked spread (i.e. raw).

In another embodiment, the composition is initially provided after it has been exposed to a temperature of 70-100 degrees Celsius for a period of 60-360 minutes and additionally exposed in matrix (e.g. comprising wheat) to a temperature of 150-250 degrees for a period of 15-60 minutes. Subsequently, the composition is provided after it has been exposed to a temperature of 70-100 degrees Celsius for a period of 60-360 minutes and additionally exposed in matrix to a temperature of 150-250 degrees for a period of 2-10 minutes. Subsequently, the composition is provided after it has been exposed to a temperature of 70-100 degrees Celsius for a period of 60-360 minutes. Subsequently, the composition is provided in the matrix without any additional heating or processing.

Each of the stapes may be carried out between 2-16 weeks, for example 2 weeks, 4 weeks, 6 weeks, 8 weeks, 12 weeks or 16 weeks.

The state of the allergenic protein in the composition may be advanced if the subject has not suffered from an adverse allergic reaction, required anti-allergy treatment, suffered from concurrent illness or received a vaccination during administration of the next stage of the treatment regimen.

If the subject has suffered from an adverse allergic reaction, received anti-allergy treatment or suffered from a concurrent illness during the next increment, then the same protein state may be maintained for at least 2, 3, 4 or additional weeks before further changing the status of the protein.

The subject may be monitored for adverse reactions as prescribed/recommended for oral food challenge procedures, following the first administration of each incremental dose of allergenic protein/conformational state of allergenic protein. For example, the subject may be assessed prior to administration and parameters such as pulse, blood pressure, peak expiratory flow rate in 1 second and oxygen saturation measured. The increased incremental dose or change in conformations protein state is then administered and the subject monitored for the development allergic symptoms and/or changes in any of the measured parameters. Allergic symptoms may be treated with conventional medication as required.

A subject may be considered not to tolerate an incremental dose or state of allergenic protein if significant allergic symptoms occur at least once, twice, three times or more times following administration of the incremental dose or state. Significant allergic symptoms include abdominal pain lasting for more than 20 minutes, wheezing, throat tightening, nausea/vomiting, rash or pruritus.

The maximum dose or final state of allergenic protein may be administered daily, every other day, 3 times weekly or at other regular intervals, for a period of at least 1 year, at least 1.5 years or at least 2 years. The final dose or final state of allergenic protein may be administered on a regular basis for many years until a state of sustained unresponsiveness is proven.

After the subject has taken the maximum dose or final state of allergenic protein daily for this period and has demonstrated good tolerance to the daily dose (e.g. no allergic reactions to doses in the past 3 months), administration of the maximum dose of allergenic protein of final state of the allergenic protein may be switched to a weekly regime. For example, the maximum dose or final state of allergenic protein may then be administered weekly for at least 2 years, at least 2.5 years or at least 3 years, etc.

Anti-allergenic protein IgE levels in a subject before treatment may be predictive of the amount of desensitization which may occur. The level of anti-allergenic protein IgE may be measured during the updosing phase/change of status phase and/or the maintenance phase of the treatment.

Anti-allergenic protein IgE may be used as a surrogate marker for clinical allergenic protein reactivity and may be indicative of the efficacy of the treatment. Typically, the level of anti-allergenic protein IgE rises initially during the treatment described herein and then gradually drops to low levels. Following the treatment, levels of anti-allergenic protein IgE may be reduced or abolished.

Alternatively, or additionally, the response to topical application of the composition of matter (i.e. the composition comprising the immature seeds) may be used as a surrogate marker for clinical allergenic protein reactivity.

The continuation of the treatment with the composition may not necessarily be dependent on the measurement or presence of food Specific IgE, but on the proof of a state of sustained unresponsiveness—i.e. the continuation of a state of tolerance to the allergenic food even after a period of non-exposure such as 1 month, 2 months or more is proven.

For example, anti-allergenic protein IgE levels may be reduced to zero, substantially zero, or very low levels.

2. Prevention/Prophylaxis

According to another aspect of the present invention there is provided a method of preventing the development of allergy to seeds by providing children the composition (either denatured or non-denatured) described herein, (e.g. as their first exposure), under conditions that prevents the development of an allergy to the seeds.

Typically, the subject of this aspect of the present invention is a human subject, younger than 18 years old. In a particular embodiment, the subject is younger than 3 years old. In another embodiment, the subject is between 6 months and 3 years old. The composition described herein is typically provided orally in a format suitable for infants—e.g. in milk formula, in baby food, in drops etc. The subject is subjected to the composition for a length of time and at a dose that prevents allergenicity. Contemplated time frames include for at least 3 months, 4 months, 6 months, 9 months, 1 year, 1.5 years, 2 years, 3 years or longer. Contemplated weekly doses of antigenic protein in the composition are between 00.05-2 mg per week, such as 0.1 mg, 0.5 mg. 1 mg or 2 mg per week.

The amount of antigen protein or conformational state of antigenic protein (as described herein above) may be increased/changed throughout the preventative procedure.

Allergy Testing

According to another aspect of the present invention there is provided a method of determining if a subject is allergic to a seed, i.e. allergy diagnosis comprising:
   (a) performing an allergy skin test by applying the composition (either denatured or non-denatured) to the skin of the subject, (e.g. by performing a small abrasion of the skin in the same area); and
   (b) analyzing the skin of the subject, wherein a non-allergenic response on the skin of the subject (absence of a wheal and flare response) is indicative that the subject is not allergic to the seed.

As used herein, the term "non-allergenic response" refers to a wheal size less than a predetermined amount e.g. 3 mM, 4 mM or 5 mM in diameter being considered to be non-allergenic.

The amount of composition used for allergy testing is typically one or two drops of a 1:10 weight/volume preparation of whole food or protein extract.

It will be appreciated that the composition of matter may be used to rule in an allergic subject, as well as to rule out a non-allergic subject. Thus, for example a subject may be ruled in as being allergic if the wheal size is greater than a predetermined amount—.g. 3 mM, 4 mM or 5 mM in diameter As used herein the term "about" refers to ±10%.

The present invention further considers corroborating the diagnosis using other traditional methods—for example using the Kallestad Allercoat EAST System (Sanofi-Pasteur Diagnostics, USA). Alternatively, testing may proceed utilising any of the EAST, Pharmacia or the UniCap systems or allergen skin prick testing.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Determination of Optimal Time for Immature Seed Harvesting

Materials and Methods

Plant material and growing conditions: Cv. 'Hanoch' was used for the hypoallergenic peanut (referred to herein as "Pronut" production). Hanoch is a Virginia-Type peanut cultivar. It is a late-maturing, spreading variety with indeterminate flowering pattern. It is characterized by "Super-Giant" seed size (>1.25 g/seed). Its seeds develop relatively slowly, enabling better discrimination between the seed developmental stages (see below). Plants were grown in ~0.3 Hectare of commercial plot in the Western Negev region, Israel. Plants were sown mechanically with 5 plants/$m^2$ spacing. Growing conditions were according standard procedures for the cultivation of peanuts as described [Gupta et al., Journal of Agricultural Science 2014 7(1)].

Identification of developmental stage: The exact seed developmental stage for Pronut production was determined based on calculating the ratio between seed diameter and pericarp average thickness (FIG. 1). This is based on the natural pod-filling process of peanut; at the beginning of the development the fertilized ovule is tiny, occupying less than 5% of the total pod volume. Later, during seed development, it expands gradually until full maturation, wherein seed occupies over 90% of the total pod volume. At this stage, the seed coat ("testa") becomes pink. As such, peanut development was divided into five groups (FIG. 1). R3/R4-0-20% seed-filling; R5-30-50% seed-filling; R5.5-50-60% seed filling; R6-70-80% seed filling/white testa; R7-<80% seed filling/pink testa.

Preparation of Pronut:

1. Harvest, sorting, storage and preservation:

Hanoch Plants were up-rooted at 71 days post planting (DPP). At this time point, the seed fraction at stages (R5, R5.5) is the highest in the sample, but all other developmental stages are also present. Pods were harvested manually. Since these pods are vulnerable they were kept fresh for further seed processing. Accordingly, they were immediately transformed to 4° C. cold room. Later, fresh seeds were manually separated from pericarps (fresh shell), sorted for each developmental stage (R4-R7) and immediately stored at −20° C.

2. Protein content determination, sample preparation and storage: 2 g/week/subject were used in the clinical trial. Protein content was determined for each developmental stage by Kjeldahl method (AOAC981.10), based on nitrogen quantity in the sample. For the clinical long-term treatment 28 g of immature R5/R5.5 (corresponding to 2 g of total proteins) were transformed to 50 ml tubes. This tube was used as the weekly treatment unit for each subject. Tubes were transferred to freeze drying process in Gamma 2-20 desiccator (Christ) for 48 h. After drying, seeds were ground by sterilized pistil and mortar and transformed back to the same 50 ml tube. This freeze-dried powder was kept at 4° C. prior to heat treatment. At this stage in the process, the composition is referred to as Pronut.

Pronut Heat Treatment: 20 ml of sterile water was added to 50 ml tubes containing dry Pronut powder equivalent to 2 grams of peanut proteins, to reach a final 1:10 wt/vol concentration. Tubes were hermetically closed and placed within a hot water tub at a temperature of 95° C. in a gentle steering apparatus, for 120 minutes. After cooling, tubes were placed for storage in freezer at −3° C. until disbursal to patients.

Skin tests: Skin prick tests are an indirect measure of cutaneous mast cell reactivity due to the presence of specific IgE antibodies. Skin testing detects allergen-specific IgE bound to mast cells. The allergen cross-links specific IgE bound on the mast cell and this causes degranulation of preformed mediators, including histamine and tryptase. Histamine release is the major mediator that results in a hive at the prick site and surrounding erythema, called a wheal and flare. All skin tests require validation, by concomitantly applying a positive control test containing 1 mg/ml of histamine base and a negative control, usually glycerinated saline. A positive test is considered as a wheal larger than 3 mm above the negative control. In the present study, a prick/puncture technique was used, involving a skin testing device pricked through droplets of allergenic extracts. The wheal and flare was measured following 15-20 minutes, the widest diameter measured in millimetres and recorded in the CRF.

Skin tests were performed with Peanut allergen extract, commercially manufactured by ALK Abello, USA, prior to and following heat treatment as detailed above and reconstituted 1:10 wt/vol powder from immature peanuts at different maturation stages prior to and following heat treatment as detailed above.

Measurement of Peanut Specific and component specific IgE and IgG in serum (Phadia): Peanut specific- and component specific-antibodies in serum were performed in the initial evaluation of all children as well as during and at the end of the Pronut treatment, via solid-phase immunoassay, Immunocap 100, Thermo Fisher Scientific Inc. Specific IGE and IgG were also measured on the same system component against the peanut specific allergenic proteins Ara h1, Ara h2, Ara h3, Ara h6 and Arah8.

Figure 2:
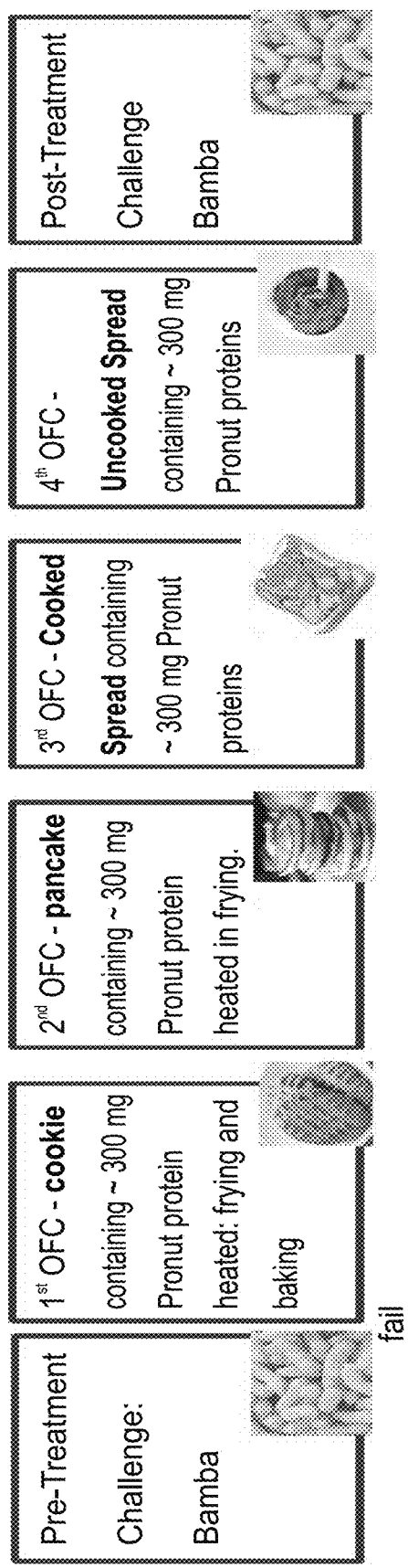
FIG. 2 illustrates the four stages of Pronut Structured Gradual Exposure (ProSGEP) protocol, according to embodiments of the present invention.

Pronut Structured Gradual Exposure Protocol (ProSGEP): ProSGEP is a 4 phased protocol (FIG. 2). Each phase begins with an observed food challenge (OFC) under allergist supervision with the tested food, and if no allergic reaction is elicited, the patient then begins a 10-12 week phase of home-based treatment during which he/she consumes daily the dose and form of Pronut that was proven safe during the challenge. In all phases of the study until the end of the protocol patients are instructed to continue avoidance of any other peanut products. All oral food challenges (OFC) are carried out in the allergy clinic under supervision after allergy diagnosis is established. OFC is with a Pronut product that was prepared by the patient's caregiver following a precise recipe detailing quantities and heating temperatures, to ensure the same product is to be ingested by the child at home after a successful OFC. If a child fails a certain OFC stage, he/she can go back to eating the last Pronut product consumed without allergic reaction. If the first OFC fails, the child can try again with a recipe containing half of the initial Pronut dose after consideration of lab tests and allergy history.

$1^{st}$ OFC Pronut Cookies Recipe
Ingredients:
   1¼ cup self-rising flour
   2 eggs
   1 cup (200 ml) milk
   1 cup sugar (white/ brown)
   ½ vegetable oil
   Content of 1 tube containing 2 gr of cooked Pronut®
Instructions:
   1. Pre heat oven to 180° C.;
   2. Mix all ingredients in 1 bowl;
   3. Pour in pan;
   4. Fry both sides until golden brown;
   5. Bake for 20 minutes;
   6. Keep refrigerated or frozen until use.

$2^{nd}$ OFC-Pronut Pancake Recipe
Ingredients:
   1¼ cup self-rising flour
   2 eggs
   1 cup (200 ml) milk
   1 cup sugar (white/brown)
   ½ vegetable oil
   Content of 1 tube containing 2 gr of cooked Pronut®
Instructions:
   1. Mix all ingredients in 1 bowl.
   2. Pour in standardized pancake pan
   3. Fry both sides until golden brown
   4. Keep refrigerated or frozen until use.

$3^{rd}$ OFC Pronut Spread Recipe (Cooked)
Ingredients:
   Content of 1 tube containing 2 gr of cooked Pronut®
   50 gr of non-dairy chocolate spread or Minced Dates spread
Instructions:
   1. Mix ingredients thoroughly
   2. Keep refrigerated no additional cooking required the cooked Pronut is provided by the allergy team. As all Pronut until this stage, a quantity equivalent to 2 gr of protein mixed with 20 CC of sterile water in a sealed, 50 ml vial, cooked at 95 degrees Celsius for a period of 2 hours prior to cooling and storage at −3 degrees.

$4^{th}$ OFC Pronut Spread Recipe (Raw)
Ingredients:
   Content of 1 tube containing 2 gr of raw Pronut®
   50 gr of non-dairy chocolate spread or Minced Dates spread
Instructions:
   1. Mix ingredients thoroughly
   2. Keep refrigerated until use Challenge procedures: All OFCs were performed by an experienced allergy team in an appropriately equipped clinic or hospital with available rescue facilities and medications.

The allergy specialist was personally responsible for the patients' follow-up during, and after the completion of the SGEP and in contact with the parents during all phases, advising in case of reactions or difficulties or questions as needed. The peanut graduated challenge timetable for each stage is provided as Tables 1-3, herein below.

TABLE 1

Peanut Graduated Challenge (Bamba ®, Osem Investments Ltd.) for the clinic trials.

| Time(h) | Challenge dose No. of Bamba ® | Cumulative | mg Peanut | POx | R | Skin/ General |
|---|---|---|---|---|---|---|
| 0:00 | ½ | ½ | 57.5 | | | |
| 0:30 | 1 | 1 | 115 | | | |
| 1:00 | 2 | 3 | 257 | | | |
| 1:30 | 4 | 7 | 609 | | | |
| 2:00 | 6 | 13 | 1130 | | | |
| 2:30 | 10 | 23 | 2000 | | | |
| 2:30 | Only follow-up | — | | | | |
| 4:00 | Only follow-up | — | | | | |

P = pulse;
R = Respiratory Rate,
Skin = skin findings i.e.: redness/itch/rash/hives/etc.

TABLE 2

Pronut Cookie/Pancake Graduated Challenge table for the clinic trials.

| Time(h) | Challenge dose cookie/pancake | Cumulative | General | P | R | Skin |
|---|---|---|---|---|---|---|
| 0:00 | ¼ | | | | | |
| 0:30 | ¼ | ½ | | | | |
| 1:00 | ½ | 1 | | | | |
| 1:30 | 1 | 2 | | | | |
| 2:00 | 1 | 3 | | | | |
| 2:30 | Only follow-up | — | | | | |
| 4:00 | Only follow-up | — | | | | |

P = pulse;
R = Respiratory Rate,
Skin = skin findings i.e.: redness/itch/rash/hives/etc.

TABLE 3

Pronut Spread Graduated Challenge table for the clinic trials.

| Time(h) | Challenge dose tea spoons | Cumulative | General | P | R | Skin |
|---|---|---|---|---|---|---|
| 0:00 | ¼ | | | | | |
| 0:30 | ¼ | ½ | | | | |
| 1:00 | ½ | 1 | | | | |
| 1:30 | 1 | 2 | | | | |
| 2:30 | Only follow-up | — | | | | |
| 4:00 | Only follow-up | — | | | | |

P = pulse;
R = Respiratory Rate,
Skin = skin findings i.e.: redness/itch/rash/hives/etc.

Inclusion Criteria:
1. Patient is more than 1 year of age with a clinical history of immediate allergy to peanuts.
2. A positive oral food challenge with an immediate allergic reaction elicited after the ingestion of 1 gr of peanut protein or less (a negative 2 gram challenge is considered proof of the absence of allergy).
3. Written informed consent is obtained—prior to first study visit.
4. There is at least a 30% reduction in skin test wheal diameter to Pronut compared to the standard peanut skin test.
5. The patient and the patient's family must be willing and committed to comply with study protocol and to remain at the clinic for the required duration during the study period.

Exclusion Criteria:

Patients are excluded from participating in this study if 1 or more of the following criteria are met:
1. A previous allergic reaction to a peanut containing food met criteria for grade 4 anaphylaxis, i.e. patient required prolonged hospitalization, intubation, IV infusion of vasopressor amines, etc.
2. The patient has another confounding underlying chronic disorder, such as: Eosinophilic gastroenteritis, Inflammatory Bowel Disease, any severe chronic underlying disease (heart, lung, neurological, etc.) except for atopy related chronic disease including atopic dermatitis, allergic rhinitis or asthma. If asthma is deemed uncontrolled by examining physician, controlling medication will be started and asthma control achieved prior to study enrolment.
3. Patients consuming 2000 mg or more of peanut proteins during the screening visit for the study without any evidence of allergic reaction.
4. The patient is expected to be poorly compliant with study product administration, study procedures, or visits.

Results

Determination of optimal date for immature seed harvesting: The most efficient time to harvest the immature seeds was determined (Table 4). Plants from Hanoch cultivar were grown in the field. Starting at 57 days post planting (DPP) plants were harvested and inspected every 3-4 days. 5 plants were sampled for each date. Pods and seeds were separated from the plant, and sorted according to their developmental stage. It was found that the most efficient time for collection is around 70 DPP. At this stage the percentage of the immature seed (R5, R5.5) is the highest (marked in bold in Table 4).

TABLE 4

Determination of optimal time for immature seeds harvesting.

| DPP | Total pod weight (g) | Total seed weight (g) | R3/R4 Weight | % | R5 Weight | % | R5.5 Weight | % | R6 Weight | % | R7 Weight | % |
|---|---|---|---|---|---|---|---|---|---|---|---|---|
| 59 | 256 | 6 | 3.5 | 58 | 2.5 | 41 | 0 | 0 | 0 | 0 | 0 | 0 |
| 63 | 395 | 21 | 4.8 | 35 | 5 | 23 | 1.5 | 7 | 6.5 | 31 | 0 | 0 |
| 67 | 494 | 28 | 9.8 | 35 | 8 | 20 | 5.8 | 20 | 4.6 | 16 | 0 | 0 |

TABLE 4-continued

Determination of optimal time for immature seeds harvesting.

| DPP | Total pod weight (g) | Total seed weight (g) | R3/R4 Weight | % | R5 Weight | % | R5.5 Weight | % | R6 Weight | % | R7 Weight | % |
|---|---|---|---|---|---|---|---|---|---|---|---|---|
| 71 | 730 | 62 | 8.5 | 14 | 17.5 | 14 | 9 | 15 | 12 | 19 | 15 | 24 |
| 74 | 850 | 79 | 2.7 | 3 | 11.9 | 15 | 18 | 25 | 31.6 | 40 | 13 | 16 |

DPP = days post planting.

Example 2

Use of X-ray Technology to Improve the Efficiency of Pronut Seed Production

One of the limiting factors of Pronut's manufacturing is the relatively low production efficiency of the embryonic seeds. For peanuts, only 2% of the harvested material in the field is at the suitable stage (R5). Also, the embryonic seeds are much more vulnerable than the mature seeds and need immediate cold storage. The necessity of manually opening each pod makes the production and sorting of seeds a very tedious and expensive task. Therefore, new production methods are needed to advance the profitability of Pronut. Here an initial study is presented demonstrating the feasibility of the usage of X-ray technology for fast and easy determination of the R5/R5.5 peanut seed stage without shelling the pod.

Figure 3A:
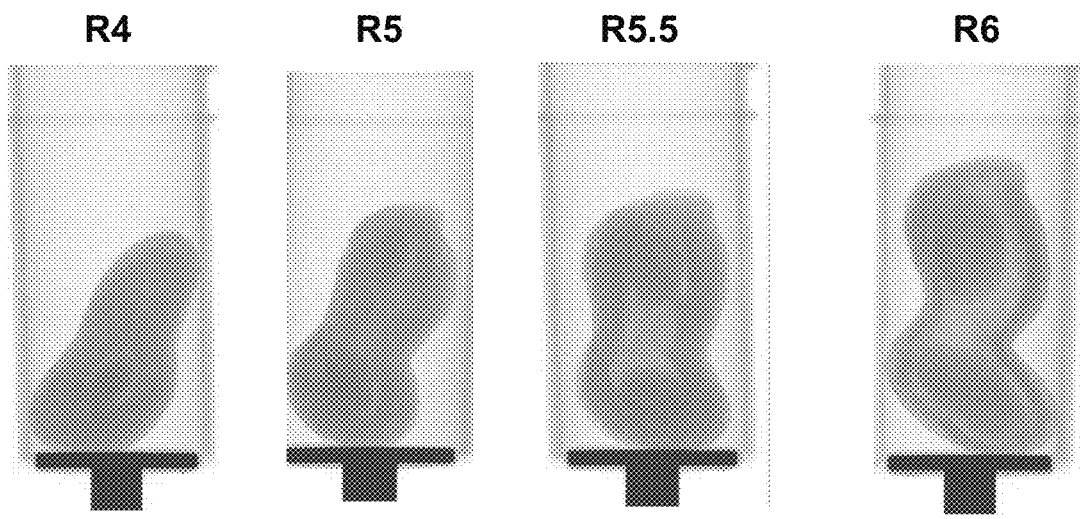
FIG. 3A demonstrates the usage of X-ray for seed stage development.
Figure 3B:
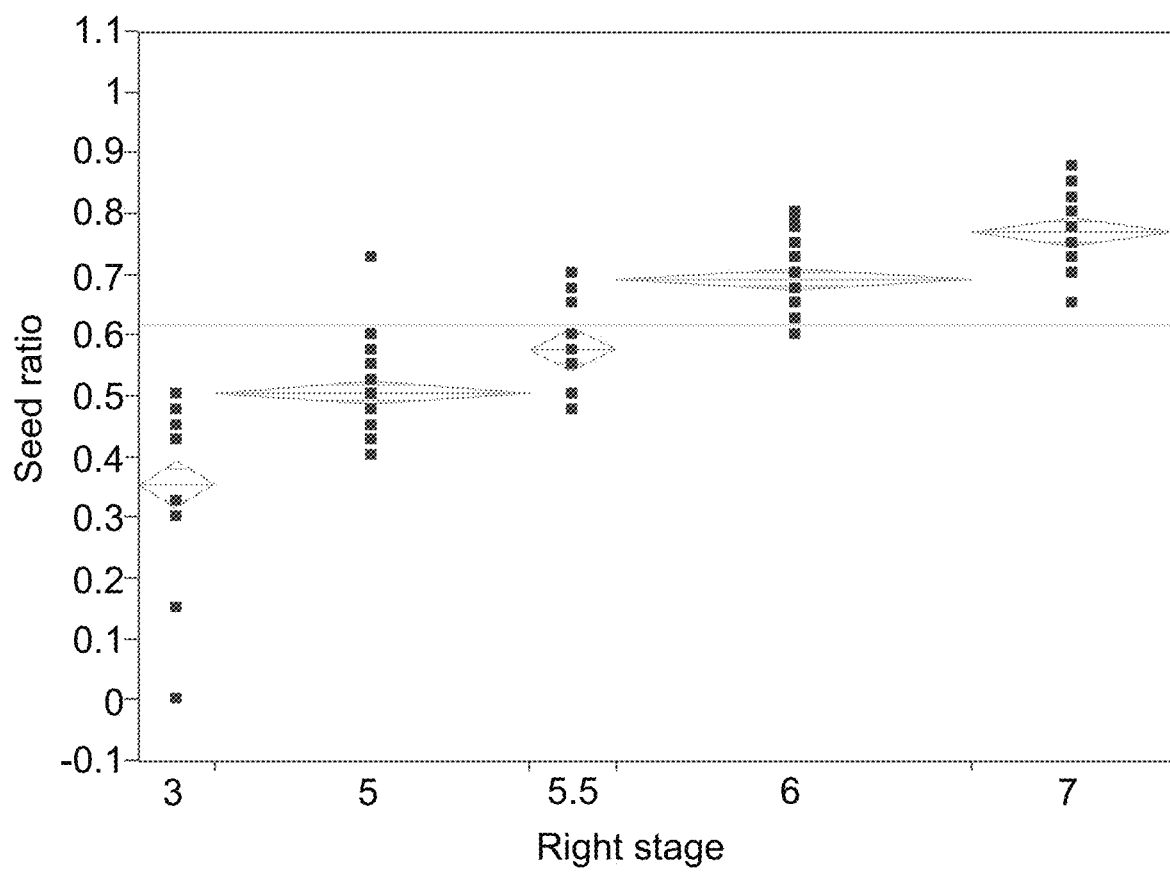
FIG. 3B illustrates the correlation between the seed ratio (calculated from the x-ray photos) and the manual determination of seed stage.

For the experiment 100 pods of cv Hanoch that were freshly harvested at 71 PPD, were subjected to x-ray exposure (FIG. 3A). Afterwards, each X-ray photo was analyzed for the seed/pod area calculation. Pods then shelled manually and the actual stage of seed development was determined. A very significant correlation was found between the calculated seed/pod ratio and the actual seed developmental stage (p<0.001), demonstrating the feasibility of the x-ray technology as a tool for pronut production (FIG. 3B).

Example 3

Predictive Value of Pronut Skin Testing in the Diagnosis of Peanut Allergy

The results of skin testing with the commercially available peanut extracts and a 1:10 solution of raw Pronut were compared with the results of oral food challenges with peanuts.

The positive predictive value of a Pronut Skin test with a wheal size of more than 5 mm is 85%—a significant improvement over the positive predictive value of the commercial peanut extract.

Example 4

Safety and Efficacy of SGEP with Pronut in the Treatment of Peanut Allergic Children 15 peanut allergic children, proven by the elicitation of immediate allergic reactions observed in an oral challenge with peanuts/Bamba® (Osem Investments Ltd), were enrolled in a prospective, open, phase I/II trial of peanut desensitization using ProSGEP.

All enrolled children were older than 1 year of age, median age at enrolment 3.8 years. Children reacted to the peanut challenge at an ingested dose, lower than or equal to 600 mg of peanut protein in the form of Bamba® (Osem).

The median dose of peanut proteins eliciting an allergic reaction in this group of children was 115 mg (1½ Bamba®). All 15 enrolled children have passed phase 1 of ProSGEP (Pronut cookies) without any allergic reaction on challenge or at home. 12 of the 15 enrolled children have passed phase 2 of ProSGEP (Pronut pancakes) without any allergic reaction on challenge or at home. 3 of the 15 enrolled children have passed phase 3 of ProSGEP (cooked Pronut spread) without any allergic reaction on challenge or at home.

Skin tests performed on the 3 children passing phase 3 SGEP show a significant reduction in the peanut skin test wheal size.

Example 5

Preliminary Demonstration of the Use of Immature Peanuts as a Diagnostic Tool

Figure 4:
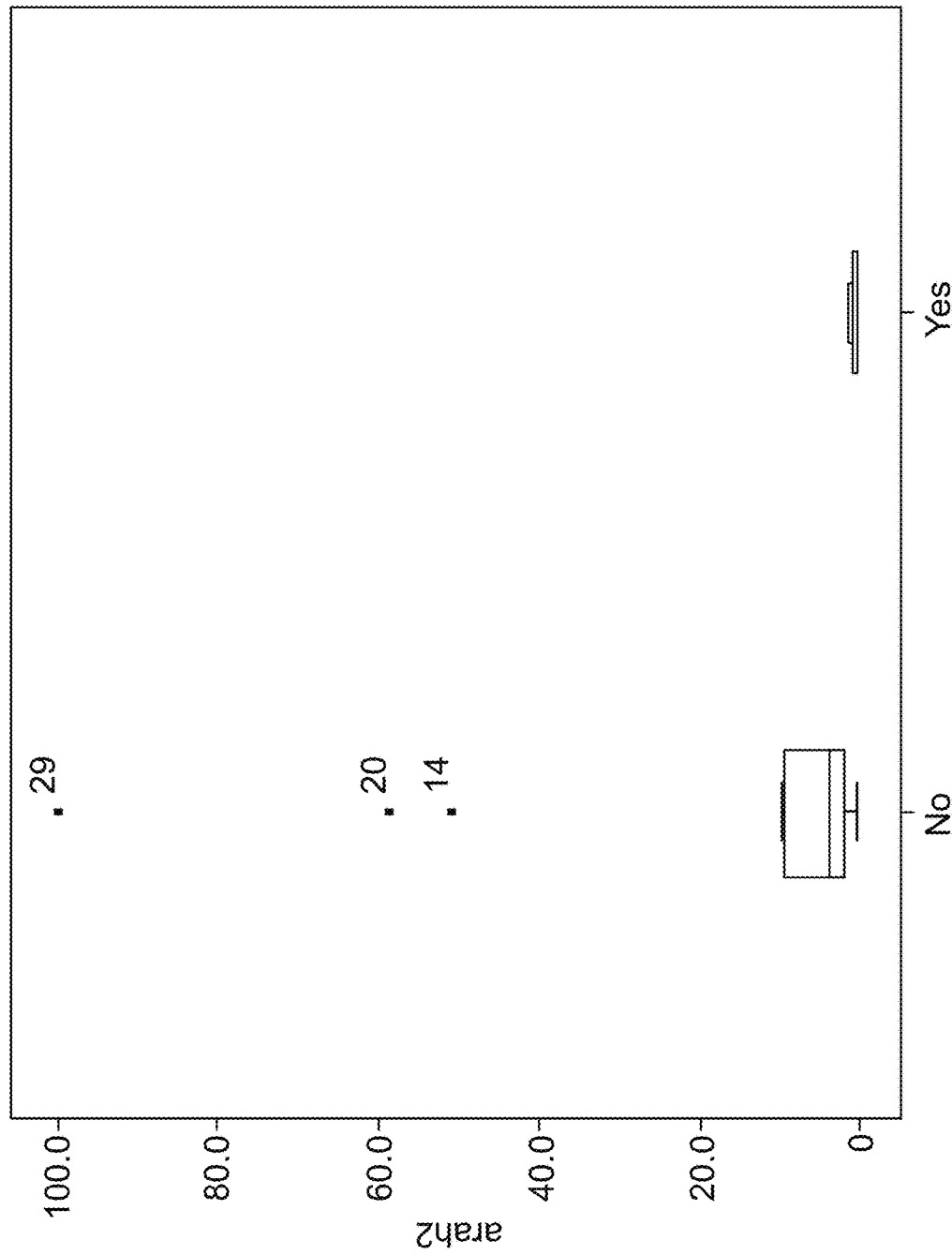
FIG. 4 is a graph illustrating the correlation between testing allergenicity using the extract from immature peanuts and by specific antibody levels against AraH2 in blood.

A skin test was performed on 24 children with appropriate history who reacted positively to a standard skin test (using mature peanut extract). The skin test included testing with peanut extract which was at stage (R5). Test results were sorted by the size of the wheal, with a size smaller than 5 mm considered to be non-allergic, and over 5 mm considered to be allergic. Of the 24 children, a group of 8 children had a very low level of antibody against AraH2 (FIG. 4), using the Pharmacia/ThermoFisher diagnostics immunocap 100 system. In other words, these eight children were mistakenly identified according to the standard methods as allergic, whereas using the immature peanut composition, they were shown to be non-allergic. Three of these children have already gone through a peanut challenge without a problem.

The trial continued over the year such that overall seventy-three preschooler subjects were enrolled in the trial. The mean age was 37 months. All subjects had a history of one or more significant allergic reactions to a peanut containing food as well as positive skin and blood tests compatible with peanut allergy, abstained completely from peanuts and carried an automated epinephrine injector at all times. Patients were challenged in a graduated peanut food test by consuming Bamba™ snack up to 2000 mg of peanut protein or until the development of objective symptoms of an allergic reaction. The last cumulative tolerated dose before the development of symptoms was recorded. Patients were divided into allergic/tolerant groups according to the result of the food challenge (1=proven true allergy; 0=tolerant). Each patient was also subjected to skin prick tests (SPT) that included "regular" commercial peanut test (alk abello 1:10 w/v peanut extract) vs. the R5 seed peanut test. The R5 test vial was made by adding 5 cc H2O (HPLC grade) to 0.5 g of lyophilized R5 seed powder, for a 1:10 protein w/v. The level of total proteins in the R5 sample was determined by the Kjeldahl (AOAC 981.10) method (AminoLab, Rehovot, Israel). The size of the SPT wheal to peanut was recorded after 15 minutes. The threshold for peanut sensitivity of the SPT was determined according to international recommendations as 3 mm wheal size, also tested according to the optimal ROC of the test at 5 mm of wheal size). The results of the SPT were compared with the food challenge test as well as with the results of specific Peanut IgE and anti Ara h2 specific IgE.

Results

Figure 5A:
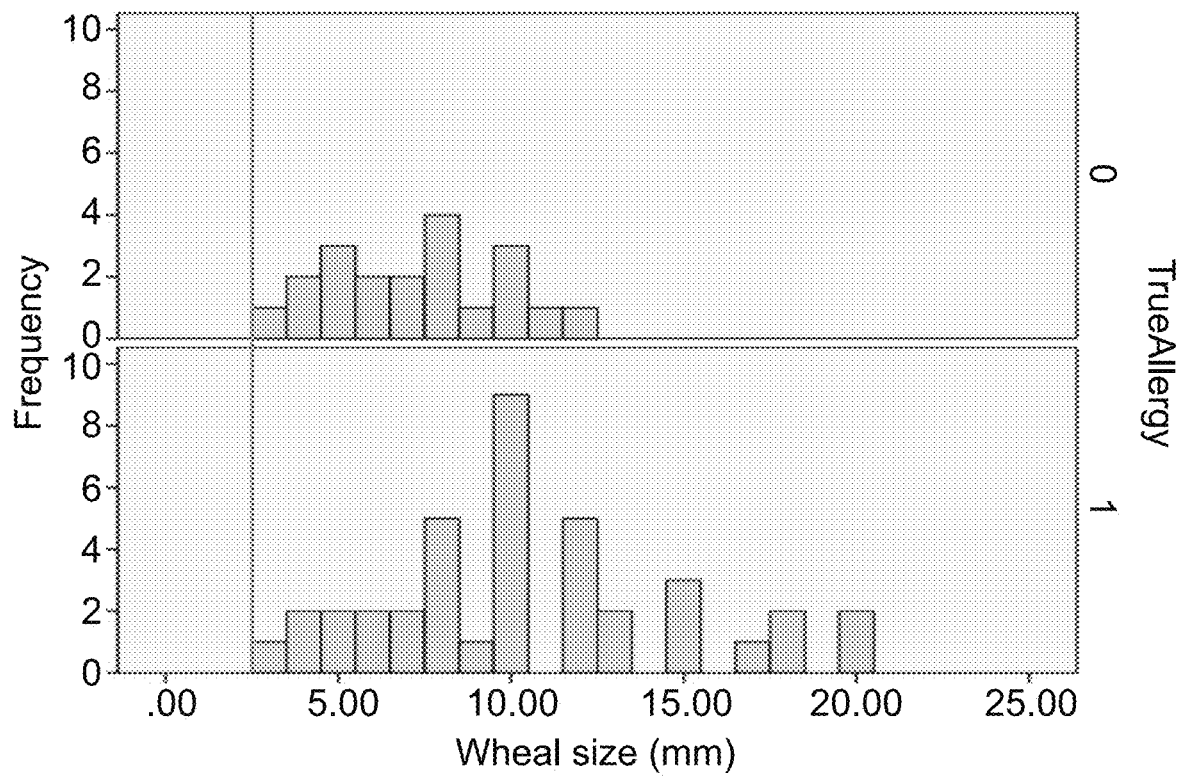
FIGS. 5A-B. Skin Prick Test (SPT) with commercial peanut (A) or with R5 peanut (B) in preschool children with (TrueAllergy=1) and without (TrueAllergy=0) challenge proven peanut allergy. Test results are provided by wheal size (mm). Cutoffs are presented by red lines.
Figure 5B:
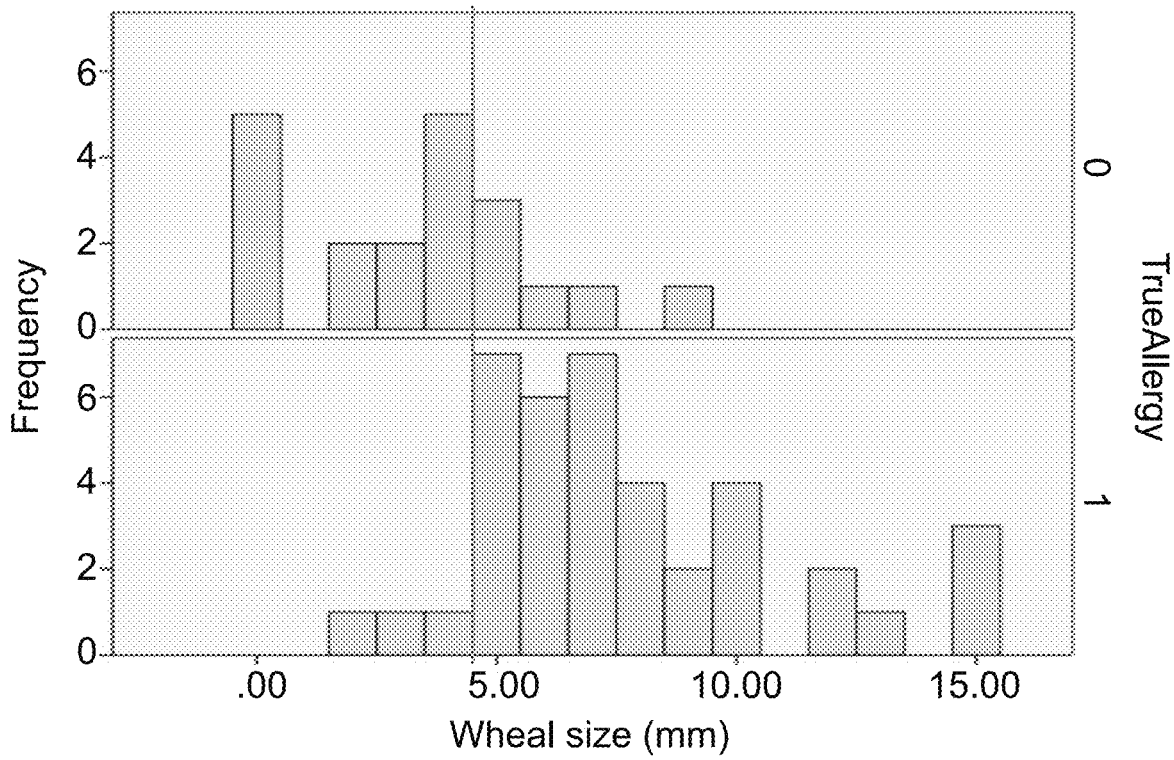
Figure 6:
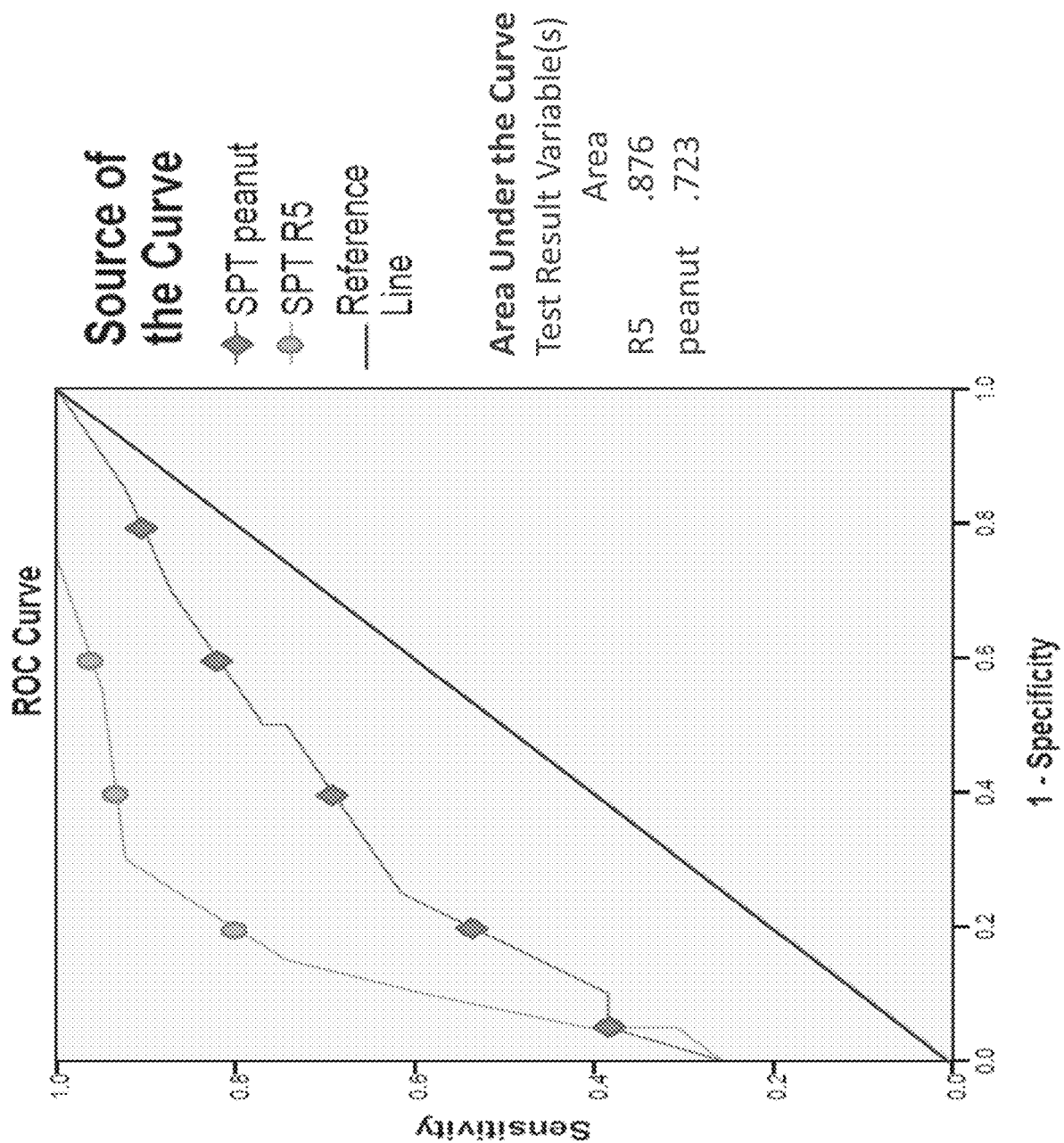
FIG. 6 is a ROC comparing SPT with commercial peanut test vs ROC of Pronut (R5) in the diagnosis of preschool peanut allergic children allergy.
Figure 7A:
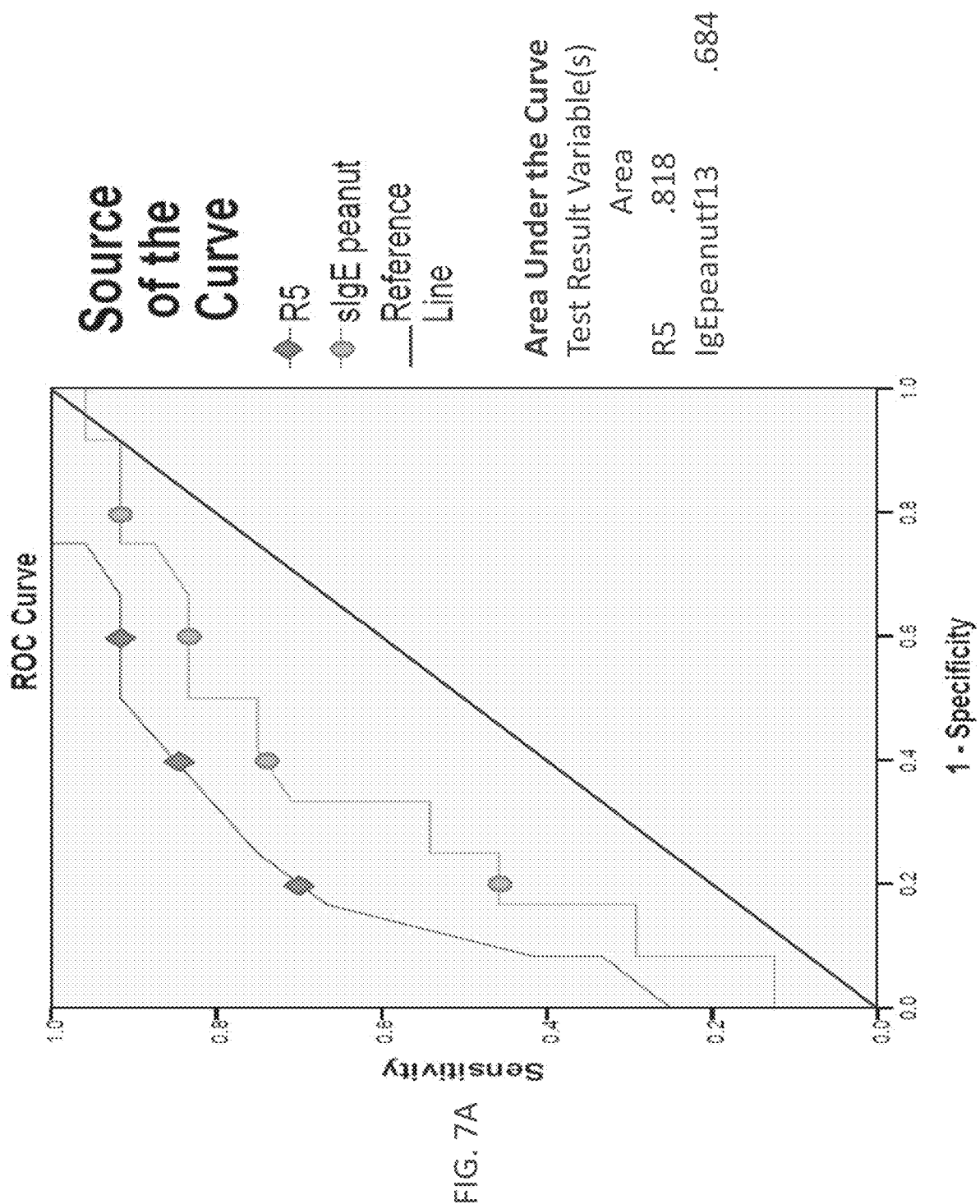
FIG. 7A is a ROC comparing SPT with Pronut (R5) with the serum level of peanut specific IgE in the diagnosis of preschool peanut allergic children allergy.
Figure 7B:
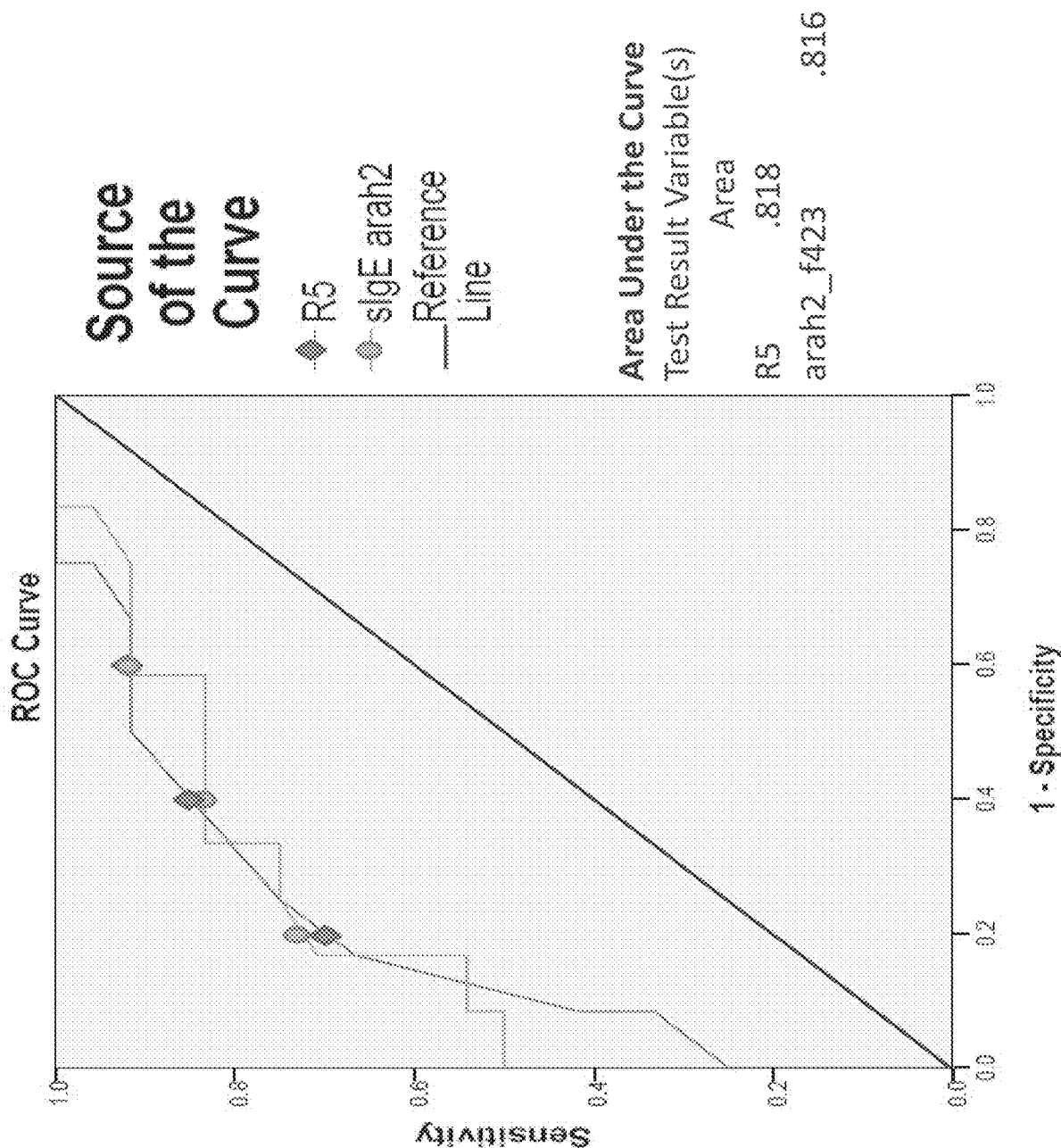
FIG. 7B is a ROC comparing SPT with Pronut (R5) with the serum level of Ara h2 specific IgE in the diagnosis of preschool peanut allergic children allergy.

The diagnostic value of the R5 seed was compared with that of the commercial peanut diagnostic kit (mature seeds) by using a skin prick test (SPT) on subjects suspected of peanut allergy. The results of the SPTs were recorded according to the "standard" peanut allergy sensitivity, determined by a food challenge test (FIGS. 5A-B). As shown, all children were diagnosed as sensitive (threshold wheal size—3 mm) in the standard peanut SPT test (FIG. 5A) irrespective of the true allergic status, where 33% of them (24 subjects) were actually proven tolerant in the peanut food challenge. In contrast, the R5 treatment found more reliable (FIG. 5B), wherein only 3 patients (out of 24) were diagnosed allergic to peanut (threshold wheal size—5 mm) and proven tolerant in the peanut food challenge.

Example 6

Testing Peanut Allergy by Skin Prick Testing 42 children with peanut allergy at an average age of 1.8 years were tested. As expected in a group of young children with allergy, 47% were found with atopic dermatitis, and 33% with asthma. The allergic reactions to peanuts in most children were skin reactions (80%), respiratory responses (24%), and gastrointestinal reactions (21%).

The average reaction to the standard peanut test was 8.9 mm (reaction above 3 mm was considered a positive reaction). The skin reaction to the standardized peanut test after cooking was unchanged from the initial response. The response to exposure to peanuts of the "Hanoch" type at the R7 stage was even higher than the standard response (12.9 mm on average), with no change before and after heat treatment. The response to exposure to peanuts of the "Hanoch" type at the R5 stage was 7 mm prior to heat treatment ith a decrease to an average of 5.8 mm after heat treatment.

On average, the skin test of immature peanuts after heat treatment showed a 33% reduction as compared to the standard test using mature peanuts and a decrease of 15% in immature peanuts without heat treatment. This experiment shows that it is possible to identify a population of children for whom the immature peanuts after heat treatment are a reduced allergen—and significantly, a reduction of at least 30% in the diameter of the skin reaction.

According to the present results out of 42 children that have been tested so far, 62% of them showed a reduced allergic reaction to the Pronut composition.

Example 7

Field Experiment to Inspect the Effect of Variety and Plant Hormone on R5 Yield

Two varieties were used in the field trial. One was 'Hanoch', the most common peanut cultivar in Israel. A second variety (referred to herein as Mona) was used which had a bunch-like growing habit. The flowering and pod set in this variety is temporally more concentrated than Hanoch, and both of the seeds within the pod are in the same developmental stage. Previous observations indicated that Mona produces significantly more R5 seeds than Hanoch when harvested on 70 days post planting.

Each variety was sown in 10 replications (plots) of 12 meters long each. Five plots were treated with the hormone Ethrel (Ethephon 39 SL (39% w/w)) at the concertation of 350 cc/Dunham. The other five were used as untreated control. In addition, each plot was further divided into two equal (6 meters) sub-plots; one was harvested at 71 days post planting and the second at 77 days post planting. From each plot, the total pod yield (g) at the day of harvest was taken. Afterwards, pods were shelled manually and R5 seeds were collected into 50 ml tubes. R5 yield was measured as the "average number of 50 ml tubes of shelled R5 seeds that could be generated per plot". The efficiency of R5 collection was calculated as the ratio between R5 yield and the total pod yield.

Results

Figure 8A:
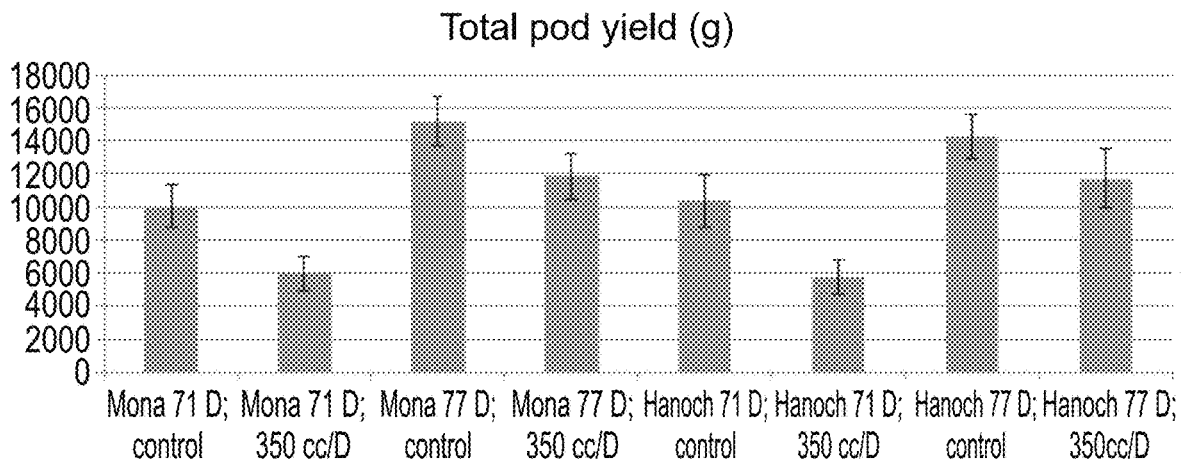
FIGS. 8A-C are graphs illustrating the difference between two peanut varieties (Mona; Hanoch) in Total Pod Yield (FIG. 8A; grams/plot), R5 Seed Yield (FIG. 8B; number of tubes per plot) and R5 Yield efficiency (FIG. 8C; %). Varieties were harvested on two dates, 71 and 77 days post planting (D). Also each variety was treated with Ethrel (350 cc/D) or not treated (control). (control).
Figure 8B:
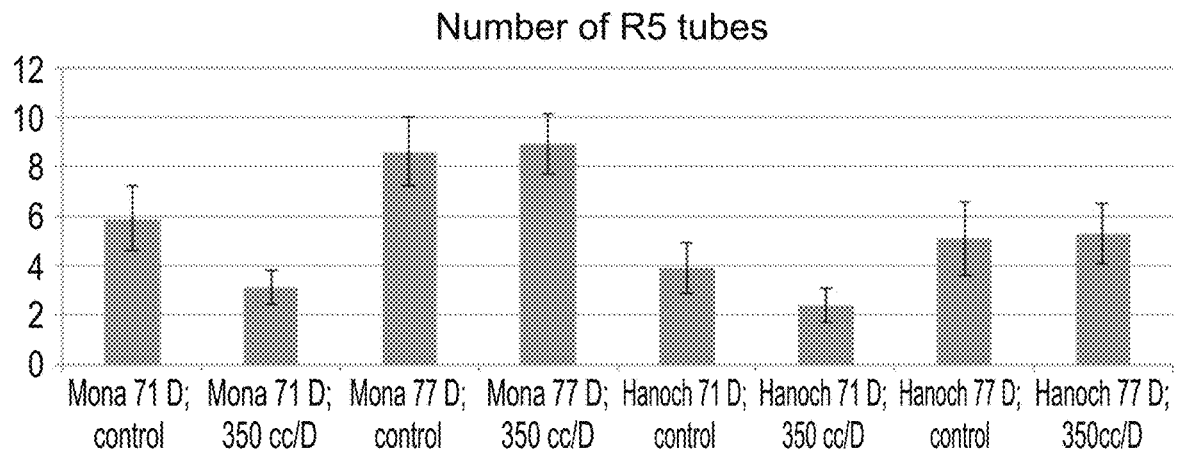
Figure 8C:
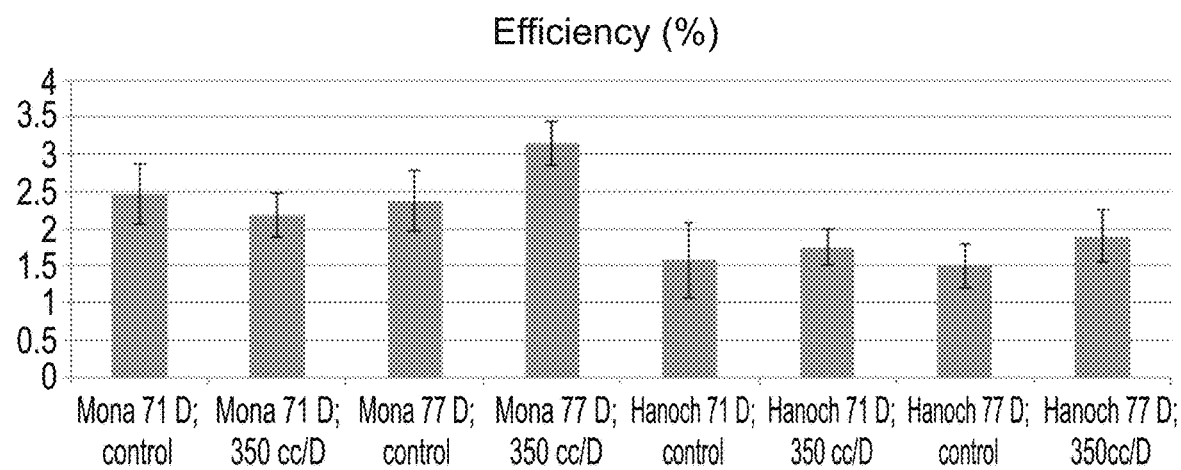

The average pod yield, number of R5 tubes and R5 production's efficiencies for each line/hormone treatment/harvest time is presented in FIGS. 8A-C. On both harvest days (71 and 77 DPA), no differences were found between Mona and Hanoch in total pod weight. Mona, however, had significantly higher R5 yield and significantly higher yield efficiency than Hanoch regardless of the harvest time or hormone treatment. Mona's best treatment (77 DPA; Ethrel 350 cc/D) had 55% more R5 yield than the best Hanoch's treatment (77 DPA; Ethrel 350 cc/D) (870 vs. 560 tubes/D, respectively). The Ethrel treatment had a positive effect on both varieties.

Figure 9:
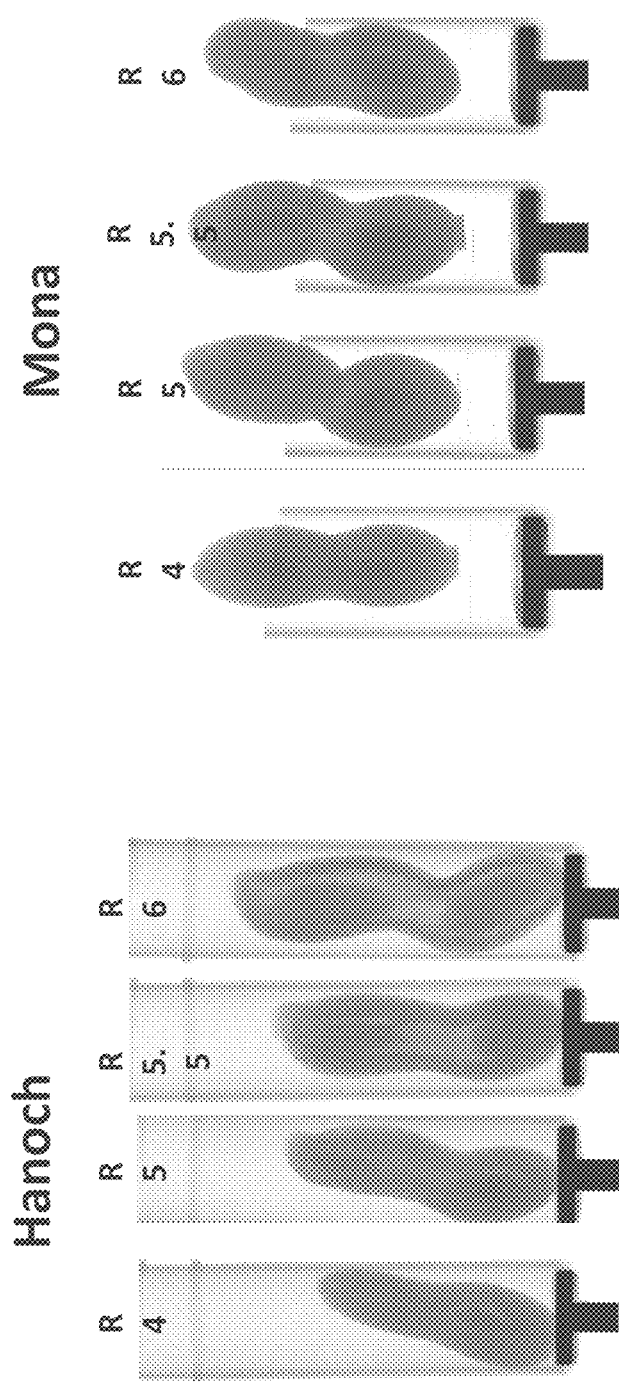
FIG. 9 are x-ray images of the two peanut varieties (Mona and Hanoch). Seed development between the lower and upper seed in Mona was more uniform than in Hanoch.

FIG. 9 illustrates that seed development was more uniform between the lower and upper seed in Mona as compared to Hanoch.

Example 8

Oral Desensitization Protocol Using R5 Seeds 12 out of 12 peanut allergic children, previously tolerating a cumulative dose of less than 350 mg of peanut protein before the development of objective allergic symptoms, are now eating between 1-4 grams of peanut protein without allergic symptoms and maintaining peanut desensitization by consuming 1-2 grams on a daily/tri-weekly basis. During the process of desensitization there were no reported adverse reactions at home or during the observed oral food challenges in any of the R5 treated patients.

Example 9

Use of Immature Seeds for the Diagnosis and Potential Treatment in Other Plant Derived Allergens, (Walnuts—*Juglandacea*)

In 10 patients with known walnut allergy, the wheal size of skin tests (SPT) using "pin-prick" with raw mature nuts was measured between 3-20 mm (median 8 mm). In the same group of patients the SPT results of testing with cooked mature walnuts showed no decrease in the wheal size, 3-22 mm (median 10 mm). Skin tests with green cooked walnuts, showed a significant reduction in wheal size, 0-5 mm (median 2 mm).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of inducing desensitization to peanut seeds in an allergic subject comprising providing a composition to the subject using a treatment regimen that induces desensitization to peanut seeds in said allergic subject, wherein the composition comprises an extract of a plurality of non-mature peanut seeds, wherein allergic proteins of said non-mature peanut seeds are amenable to heat denaturation and are denatured by heating to a temperature between 50-500° C., wherein said non-mature peanut seeds are at a developmental stage whereby the peanut seeds occupy between 40-60% of the pod volume, said composition of matter being devoid of fully mature peanut seeds.

2. The method of claim 1, wherein said composition is provided orally.

3. The method of claim 2, wherein said treatment regimen comprises initially providing said composition as a cooked product.

4. The method of claim 3, wherein said treatment regimen subsequently comprises providing said composition as a raw product if the subject displays tolerance to said cooked product.

5. The method of claim 1, wherein the subject is selected for treatment by evaluating the response to topical application of said composition.

6. The method of claim 1, wherein said composition is provided in an amount between 0.1-2 gm of protein per week.

7. The method of claim 1, wherein said subject is an infant.

8. The method of claim 7, wherein said composition is a milk formula or baby food.

* * * * *